(12) United States Patent
Liu et al.

(10) Patent No.: US 12,096,968 B2
(45) Date of Patent: Sep. 24, 2024

(54) CHEMICAL ABLATION APPARATUS FOR TREATING ARRHYTHMIA

(71) Applicant: SUZHOU SINUS MEDICAL TECHNOLOGIES CO., LTD, Jiangsu (CN)

(72) Inventors: Xingpeng Liu, Beijing (CN); Jun Mao, Beijing (CN); Mingdong Zhang, Bethesda, MD (US)

(73) Assignee: SUZHOU SINUS MEDICAL TECHNOLOGIES CO., LTD., Jiangsu (CN)

( * ) Notice: Subject to any disclaimer, the term of this patent is extended or adjusted under 35 U.S.C. 154(b) by 1278 days.

(21) Appl. No.: 16/338,095

(22) PCT Filed: Jun. 26, 2017

(86) PCT No.: PCT/CN2017/089998
§ 371 (c)(1),
(2) Date: Jul. 6, 2020

(87) PCT Pub. No.: WO2018/076738
PCT Pub. Date: May 3, 2018

(65) Prior Publication Data
US 2021/0022789 A1     Jan. 28, 2021

(30) Foreign Application Priority Data
Oct. 27, 2016   (CN) .......................... 201610959301.6

(51) Int. Cl.
*A61B 18/06* (2006.01)
*A61B 17/00* (2006.01)
(Continued)

(52) U.S. Cl.
CPC ........... *A61B 18/06* (2013.01); *A61M 25/007* (2013.01); *A61M 25/0074* (2013.01);
(Continued)

(58) Field of Classification Search
CPC .. A61M 5/348; A61M 5/158; A61M 25/0084; A61M 25/0067;
(Continued)

(56) References Cited

U.S. PATENT DOCUMENTS

| 3,746,002 A | * | 7/1973 | Haller | ................. | A61B 17/282 |
| | | | | | 24/518 |
| 5,005,754 A | * | 4/1991 | Van Overloop | ..... | A61B 17/072 |
| | | | | | 227/178.1 |

(Continued)

FOREIGN PATENT DOCUMENTS

CN     201019803 Y  *  2/2008
CN     101856271 A     10/2010
(Continued)

OTHER PUBLICATIONS

Extended European Search Report received in European Patent Application No. 17866206.0; dated Oct. 18, 2019 (6 pages).
(Continued)

*Primary Examiner* — Jason E Flick
*Assistant Examiner* — Adam J. Cermak
(74) *Attorney, Agent, or Firm* — Finnegan, Henderson, Farabow, Garrett & Dunner, LLP

(57) ABSTRACT

The disclosure relates to a chemical ablation apparatus for treating arrhythmia. The apparatus includes a clamp body, a clamp head consisting of a pair of clamp jaws, a needle head assembly, a needle head extension and retraction control assembly, pipeline components, and an electrocardiographic mapping component. The chemical ablation apparatus can control needle heads to extend out of or retract into the clamp head by means of the needle head extension and retraction control assembly. A chemical ablation reagent may be injected to a cardiac muscle tissue to conveniently achieve complete ablation of the cardiac muscle tissue by (Continued)

applying a chemical ablation method. The ablation effect can be verified by an electrocardiographic mapping system, to increase the success rate and lower the difficulty level of arrhythmia ablation operations, while also reducing the manufacturing cost of ablation apparatus and corollary equipment thereof, and decreasing expenses for atrial fibrillation surgical operations.

24 Claims, 12 Drawing Sheets

(51) Int. Cl.
 *A61B 17/29* (2006.01)
 *A61B 17/34* (2006.01)
 *A61B 18/00* (2006.01)
 *A61M 25/00* (2006.01)
(52) U.S. Cl.
 CPC ............... *A61B 2017/00539* (2013.01); *A61B 2017/00544* (2013.01); *A61B 2017/2926* (2013.01); *A61B 2017/3409* (2013.01); *A61B 17/3478* (2013.01); *A61B 2018/00351* (2013.01); *A61B 2018/00577* (2013.01); *A61M 2025/0087* (2013.01)
(58) Field of Classification Search
 CPC .. A61M 2025/0087; A61M 2025/0079; A61B 17/3478; A61B 2017/00539; A61B 2017/00544
 See application file for complete search history.

(56) References Cited

U.S. PATENT DOCUMENTS

| | | | | |
|---|---|---|---|---|
| 5,019,045 A * | 5/1991 | Lee | .................. | A61M 5/347 604/218 |
| 5,354,279 A * | 10/1994 | Hofling | ............. | A61M 25/0084 604/173 |
| 5,425,705 A * | 6/1995 | Evard | ............. | A61B 17/06061 604/36 |
| 5,693,029 A * | 12/1997 | Leonhardt | ............. | A61M 29/02 604/523 |
| 6,161,543 A * | 12/2000 | Cox | .................. | A61B 18/1492 606/41 |
| 6,638,246 B1 * | 10/2003 | Naimark | ............... | A61M 25/10 604/103 |
| 8,585,736 B2 * | 11/2013 | Horner | ............... | A61B 18/1445 606/51 |
| 9,072,522 B2 * | 7/2015 | Morejohn | ............. | A61B 18/06 |
| 9,108,030 B2 * | 8/2015 | Braga | ............... | A61M 37/0015 |
| 9,352,085 B2 * | 5/2016 | Takagi | .................. | A61M 5/158 |
| 10,849,879 B2 * | 12/2020 | Seward | .................... | A61P 5/50 |
| 2002/0002372 A1 * | 1/2002 | Jahns | .................. | A61B 18/1492 604/35 |
| 2002/0120267 A1 * | 8/2002 | Phan | .................. | A61B 18/1445 606/205 |
| 2003/0114850 A1 * | 6/2003 | McClurken | ........ | A61B 18/1442 606/50 |
| 2004/0162521 A1 * | 8/2004 | Bengtsson | ........... | A61B 5/1518 604/173 |
| 2005/0125013 A1 * | 6/2005 | Kessler | .................. | A61B 17/30 606/205 |
| 2006/0041243 A1 * | 2/2006 | Nayak | ................ | A61B 17/0206 604/173 |
| 2007/0038181 A1 * | 2/2007 | Melamud | ........... | A61B 17/3478 606/186 |
| 2008/0077165 A1 * | 3/2008 | Murphy | ......... | A61B 17/320725 604/103.05 |
| 2012/0130366 A1 * | 5/2012 | Carroll | .................... | A61B 34/73 606/41 |
| 2012/0323232 A1 * | 12/2012 | Wolf | ........................ | A61N 1/40 606/1 |
| 2013/0053822 A1 | 2/2013 | Fischell et al. | | |
| 2013/0338632 A1 * | 12/2013 | Kaplan | .................... | A61P 43/00 604/173 |
| 2014/0052067 A1 * | 2/2014 | Sausse | ............... | A61M 37/0015 604/173 |
| 2014/0303665 A1 * | 10/2014 | Gerrans | ......... | A61B 17/320725 606/192 |
| 2015/0257839 A1 * | 9/2015 | Vause | .................. | A61B 17/221 606/130 |
| 2017/0007324 A1 * | 1/2017 | Kadamus | ............. | A61B 5/6847 |
| 2017/0049450 A1 * | 2/2017 | Foerster | ................. | A61B 17/11 |
| 2018/0303414 A1 * | 10/2018 | Toth | .................... | A61N 1/36135 |
| 2021/0022789 A1 * | 1/2021 | Liu | ........................ | A61B 5/282 |
| 2024/0050143 A1 * | 2/2024 | Wolf | .................... | A61B 18/085 |
| 2024/0099759 A1 * | 3/2024 | Swanson | ................ | A61B 18/10 |
| 2024/0138896 A1 * | 5/2024 | Azamian | ................ | A61B 18/02 |

FOREIGN PATENT DOCUMENTS

| | | | |
|---|---|---|---|
| CN | 103169510 A | * | 6/2013 |
| CN | 103251451 A | | 8/2013 |
| CN | 106422041 A | | 2/2017 |
| CN | 206777607 U | | 12/2017 |

OTHER PUBLICATIONS

International Search Report for International Application No. PCT/CN2017/089998 from the State Intellectual Property Office of the P.R. China, dated Sep. 30, 2017.

* cited by examiner

CHEMICAL ABLATION APPARATUS FOR TREATING ARRHYTHMIA

CROSS-REFERENCE TO RELATED PATENT APPLICATIONS

This application is a U.S. national stage entry under 35 U.S.C. § 371 of International Application No. PCT/CN2017/089998, filed Jun. 26, 2017, which claims the benefit of Chinese Patent Application No. 201610959301.6, filed Oct. 27, 2016, both of which are hereby incorporated by reference in their entireties.

TECHNICAL FIELD

The present invention relates to a surgical instrument for treating and mapping arrhythmia, and in particular, a chemical ablation apparatus for chemically ablating cardiac muscle tissue.

BACKGROUND

Arrhythmia is a series of diseases of heartbeat losing its intrinsic rhythm due to various reasons, its incidence is high and it is extremely harmful to health. For example, the most common type of persistent arrhythmia in clinic is atrial fibrillation (AF), which is rapid and irregular contraction of atria and ventricles, caused by abnormal changes in the electrophysiological properties of atrial myocytes due to various pathogenic factors. Its patients suffer from uncomfortable symptoms such as palpitations, shortness of breath, fatigue. It increases incidence of adverse events such as heart failure, thromboembolism and death. At present, the total prevalence of atrial fibrillation in China is 0.77%, based on which the total number of patients with atrial fibrillation in China is estimated to be close to 10 million, ranking first in the world. And the prevalence of atrial fibrillation increases significantly with age, and the prevalence in the over-80-year-old age group is as high as 7.5%. With the aging of today's society, the prevalence of atrial fibrillation increases with each passing day, seriously affecting the health of people. Other examples are ventricular tachycardia (VT) and ventricular fibrillation (VF), which are excessively fast frequency of ventricular contraction, caused by abnormalities in ventricular local electric activities due to ventricular myocyte disease. Their patents cannot maintain normal blood pressure, and may even cause sudden cardiac death. Their suddenness and seriousness of onset have caused great harm to the lives and health of people.

In recent years, with the gradual recognition of the pathogenesis of atrial fibrillation, most atrial fibrillation has been found to be related to abnormal electric activities originating from pulmonary vein. The intervention of the joint between pulmonary vein and left atrium (also known as pulmonary vein antrum) by various means causes coagulative necrosis to the joint, leading to the electrical isolation formed between the pulmonary vein and the left atrium which can terminate or stop relapse of most atrial fibrillation. Surgical operations using radiofrequency energy to ablate pulmonary vein antrum through epicardium have also achieved good therapeutic results. Likewise, coagulative necrosis or electrical isolation of local ventricular myocytes with lesion by various means can prevent ventricular tachycardia and ventricular fibrillation.

Bipolar radio-frequency ablation clamps currently used in surgical operations can ablate atrial tissue touched by electrodes on clamp jaws after it is clamped on pulmonary vein antrum, but at the mouth of the clamp jaws and between the bottom of the clamp jaws on both sides, part of the atrial tissues cannot reach the electrodes, which leads to discontinuous and incomplete pulmonary vein antrum ablation, leaving the potential for electrical isolation "gap" and new atrial arrhythmia after radiofrequency ablation operations. The existing bipolar radio-frequency ablation clamps release radiofrequency energy by closely touching epicardium, which makes it difficult to form transmural damage to thicker ventricular walls, and thus having little effect on ventricular arrhythmia. Moreover, the existing bipolar radiofrequency ablation clamps cannot map whether a continuous and complete ablation line is formed at an ablation site and whether a gap is left after an ablation is completed, such that the operation effect cannot be verified during the operation, leaving hidden dangers of recurrence of arrhythmia. In addition, currently used bipolar radio-frequency ablation clamps are all imported, complex in structure and expensive in cost, requiring a series of ancillary equipment such as radio-frequency energy generators, which makes surgical operation treatment of atrial fibrillation costly and makes it impossible for some hospitals to carry out this treatment.

Chinese Invention Patent No. 201110429592.5 discloses a chemical ablation apparatus for treating atrial fibrillation. But in actual operation, when ablation clamps are placed and clamped on target ablation site, injection needle heads on the ablation clamps may damage surrounding tissues, including atrial or pulmonary vein walls, causing bleeding. In addition, this chemical ablation apparatus does not verify the effect of ablation.

SUMMARY OF INVENTION

With respect to the above technical problems, it is provided in the present invention a chemical ablation apparatus, comprising a clipping component, a needle head component and pipeline components;

the clipping component comprises a clamp body and a clamp head consisting of a pair of clamp jaws installed on the clamp body, the clamp head clamps or releases target ablation tissue by the relative motion of the clamp jaws;

the needle head component is installed inside the clamp jaws, and the needle head component comprises a needle head assembly and a needle head extension and retraction control assembly, the needle head assembly comprises an ablation reagent injection head and a plurality of needle heads installed on the ablation reagent injection head that are used to inject ablation reagents into target ablation tissue, the needle head extension and retraction control assembly controls the needle heads to extend out of or retract into the clamp jaws, and injection needle holes are provided on the side of each clamp jaw opposite to the other clamp jaw for the needle heads to extend out of or retract into the clamp jaws;

the pipeline components comprise ablation reagent transporting pipelines that are in fluid communication with the needle head assembly so as to transport ablation reagents.

Preferably, the needle head extension and retraction control assembly controls the needle heads to extend out of or retract into the clamp jaws by air pressure or hydraulic pressure.

As a preferred embodiment of the above solution, the needle head extension and retraction control assembly comprises an air bag or a liquid bag arranged on one side of the ablation reagent injection head that is distal from the injection needle holes, and an elastic component arranged between the ablation reagent injection head and the injection needle holes;

the volume of the air bag or liquid bag is changed by charging and discharging air or liquid, causing the ablation reagent injection head to move towards or away from the injection needle holes;

the elasticity of the elastic component tends to cause the ablation reagent injection head to move away from the injection needle holes.

Preferably, the needle head extension and retraction control assembly controls the needle heads to extend out of or retract into the clamp jaws by an electronic machinery.

As a preferred embodiment of the above solution, the needle head extension and retraction control assembly comprises an electromagnetic elastic component arranged between the ablation reagent injection head and the injection needle holes, the length of which is controlled with electric current so as to cause the ablation reagent injection head to move towards or away from the injection needle holes.

Preferably, the needle head extension and retraction control assembly comprises an electric motor arranged inside the clamp jaws, the electric motor causing the ablation reagent injection head to move towards or away from the injection needle holes with a transmission device.

More preferably, the transmission device is a threaded rod or a gear.

Preferably, the chemical ablation apparatus according to the present invention further comprises a cushion which is arranged on the clamp jaws and covers the injection needle holes, the thickness of the cushion being equal to or greater than the length of the injection needle heads in full extension.

Preferably, the ablation reagent transporting pipelines gradually expand in shape at the side where the ablation injection head is connected.

More preferably, a distributing board is arranged at the expanded part of the ablation reagent transporting pipeline to balance the pressure of liquids in each of the needle heads.

Preferably, each of the needle heads has an independent pipeline at least on the side of the ablation reagent transporting pipeline that is proximal to the needle head, the independent pipeline supplying to one or more said needle heads separately.

Preferably, the needle heads are installed on the ablation reagent injection head with needle fixing holes, the depth at which the needle heads are installed into the needle fixing holes can be adjusted as needed.

More preferably, the rear of the needle heads and the needle fixing holes are shaped with multiple-step structures that match with each other, so as to achieve the adjustment of the installation depth.

Preferably, the rear of the needle heads and the needle fixing holes are shaped with threads that match with each other, so as to achieve the adjustment of the installation depth.

Preferably, the head ends of needle tips of the needle heads are enclosed within holes arranged beneath the head ends.

Preferably, the chemical ablation apparatus according to the present invention also comprises an electrocardiographic mapping component, by which the conduction condition of electrocardiosignals and/or external electrical stimulus signals around the target ablation tissue is detected.

More preferably, the electrocardiographic mapping component comprises mapping electrodes and wires that connect the mapping electrodes to an electrocardiographic measurement device, which detects the conduction condition of electrocardiosignals and/or external electrical stimulus signals around the target ablation tissue.

More preferably, the mapping electrodes are arranged on the clamp jaws and are close to the injection needle holes.

Preferably, the angle between the clamp jaws and the clamp body can be adjusted.

More preferably, the clamp head and the clamp body are connected by a rotatable damping component.

As another preferred embodiment of the present invention, the clamp head is connected to the clamp body by a rotatable component with a transmission device, which can control the motion of the rotatable component under the effect of external force.

Preferably, the chemical ablation apparatus according to the present invention also comprises a spraying system and a suction system.

More preferably, the spraying system and the suction system comprises spraying holes and suction holes arranged on the clamp jaws, which are connected to a spraying pipeline and a suction pipeline respectively.

Preferably, the chemical ablation apparatus according to the present invention also comprises a pulley, around which the pipeline components and/or the wires are wound, the extension or retraction of the pipelines and/or the wires in the clamp body can adjusted by decreasing or increasing the number of times of winding of the pipeline components and/or the wires to adapt to the motion of the clamp head.

Preferably, the chemical ablation apparatus according to the present invention also comprises a fence. The fence is located on both sides of the needle holes on the clamp jaws and also at the end of the distal end of the clamp jaws and extending in the same direction as the needle heads do.

Specifically, the chemical ablation apparatus according to the present invention comprises a clipping component, a needle head component and pipeline components.

The clipping component comprises a clamp body and a clamp head consisting of a pair of clamp jaws installed on the clamp body, the clamp head and the clamp body may be provided as a whole or be provided being independent from each other, able to be assembled and disassembled; the clamp head clamps and releases target ablation tissue by the relative motion of the clamp jaws;

the needle head component is installed inside the clamp jaws, and the needle head component comprises a needle head assembly and a needle head extension and retraction control assembly, the needle head assembly comprises an ablation reagent injection head and a plurality of needle heads installed on the ablation reagent injection head that are used to inject ablation reagents into target ablation tissue, the needle head extension and retraction control assembly controls the needle heads to extend out of or retract into the clamp jaws, the injection needle holes are provided on the side of each clamp jaw opposite to the other clamp jaw for the needle heads to extend out of or retract into the clamp jaws;

the pipeline components comprise ablation reagent transporting pipelines that are in fluid communication with the needle head assembly so as to transport the ablation reagent.

The clipping component of the chemical ablation apparatus according to the present invention comprises a clamp body and a clamp head consisting of a pair of clamp jaws (distal-side clamp jaw and proximal-side clamp jaw)

installed on the clamp body, the clamp head clamps or releases target ablation tissue by the relative motion of the clamp jaws.

In the chemical ablation apparatus according to the present invention, injection needle holes are arranged on the inner side (distal side) of the proximal-side clamp jaw and on the inner side (proximal side) of the distal-side clamp jaw, the needle heads extending out of or retracting into the clamp jaws through injection needle holes. Injection needle holes on the proximal-side clamp jaw and the distal-side clamp jaw may be arranged along the long axis of the ablation reagent transporting pipelines with the same spacing in one row, two or multiple staggered rows, i.e., needle heads extending out of the clamp jaws are arranged along the long axis of the ablation reagent transporting pipeline with the same spacing in one row, two or multiple staggered rows. The purpose of this design is to reduce or avoid the incidence of "gap" after cardiac muscle tissue undergoes chemical ablation. In general, it is optimal that the damage areas caused by chemical ablation reagents injected by each needle head and its adjacent needle head overlap exactly at the border, but since the damage areas are assumed to be approximately spherical, there may be a "blind spot" not reached by chemical reagents and free of myocardium damage in the case of a small number of needle heads. So, it is preferable that the damage areas caused by two adjacent needle heads overlap, for example 1-50%, such as 5-30%, 10-30%, 15-30%, 1-20%, 5-20%, 10-20%, etc. In this sense, sometimes it is preferable to arrange needle heads in two or multiple staggered rows, where overlapped range of damage areas caused by two adjacent needle heads in one row or adjacent needle heads in two rows may be smaller, for example, 1-30%, preferably 1-20%, 5-20%, 10-20%, etc. However, the two- or multiple-staggered-row design is not always preferable. In order to optimize and simplify the design of the chemical ablation apparatus according to the present invention, or where the only need is to achieve the absence of a "gap" or "blind spot" and provide a high degree of ablation is not necessary, the treatment goal can be achieved by a single row design and by controlling the flow rate and pressure in an ablation reagent supply device. Therefore, the above examples do not set limit on the present invention.

Therefore, where needle holes on the proximal-side clamp jaw and the distal-side clamp jaw are arranged with the same spacing in one row, i.e., needle heads extending out of clamp jaws are arranged with the same spacing in one row, the spacing is arranged such that damage areas in tissue caused by chemical ablation reagents injected by two adjacent needle heads are able to overlap at least 1-40%, preferably 5-30%, and optimally 10-30%.

Where needle holes in the proximal-side clamp jaw and the distal-side clamp jaw are separately arranged in two staggered rows along the long axis of the pipeline components, i.e., needle heads extending out of clamp jaws are arranged in two staggered rows along the long axis of the pipeline components, the spacing between two adjacent needle heads in each row is the same and is set such that the damage areas in tissue caused by chemical ablation reagents injected by two adjacent needle heads in that row are able to overlap at least 1-30%, preferably 5-20%, and optimally 10-20%, and the spacing between one needle head in one row and its adjacent needle head in the other row is the same and is set such that the damage areas in tissue caused by a chemical ablation reagent injected by the two needle heads are able to overlap at least 1-30%, preferably 5-20%, and optimally 10-20%.

Where injection needle heads in the proximal-side clamp jaw and the distal-side clamp jaw are arranged in multiple rows along a long axis of the pipeline system in a staggered way separately, i.e., needle heads extending out of the clamp jaws are arranged in multiple rows along a long axis of the pipeline components in a staggered way, the spacing between two adjacent needle heads in each row is the same and is set such that the damage areas in tissue caused by a chemical ablation reagent injected by two adjacent needle heads in that row are able to overlap at least 1-30%, preferably 5-20%, and optimally 10-20%, and the spacing between one needle head in one row and its adjacent needle head in another row is the same and is set such that the damage areas in tissue caused by chemical ablation reagents injected by the two needle heads are able to overlap at least 1-30%, preferably 5-20%, and optimally 10-20%.

In one preferred embodiment, a spraying system and a suction system may be provided around every injection needle hole in the proximal-side clamp jaw and the distal-side clamp jaw, the spraying system and the suction system comprises spraying holes and suction holes arranged on clamp jaws, which are connected to a spraying pipeline and a suction pipeline respectively. For example, normal saline may be sprayed from the spraying holes and the suction holes absorb liquids around them by negative pressure, so when needle heads are injecting chemical ablation reagents, once chemical ablation reagents leak, they can be diluted by normal saline immediately and absorbed by the suction system, causing no damage to surrounding cardiac muscle tissue.

In a preferred embodiment, the distal-side clamp jaw is fixed and the proximal-side clamp jaw can slide towards the distal-side clamp jaw, the sliding of the proximal-side clamp jaw can be achieved by pushing a pushrod towards the distal end of the chemical ablation apparatus.

In another preferred embodiment, the proximal-side clamp jaw is fixed and the distal-side clamp jaw can slide towards the proximal-side clamp jaw, the sliding of the distal-side clamp jaw can be achieved by pulling a pushrod towards the proximal side of the chemical ablation apparatus.

In another preferred embodiment, clamp jaws on both sides can slide to come close to or away from each other, their sliding can be achieved by a pushrod of the chemical ablation apparatus.

In another preferred embodiment, the proximal-side clamp jaw and the distal-side clamp jaw are both arc-shaped, the radians of which may be the same as each other or match with each other so as to clamp tissue in need of ablation when the two clamp jaws touch or move towards each other.

The relative motion of clamp jaws can be controlled by known technical means, for example, a clamp body, a clamp handle, and a pushrod can be used to control the relative motion of clamp jaws, and other known techniques can also be used to control the motion of clamp jaws.

In one preferred embodiment, moving and occluding clamp jaws on both sides may be achieved by the methods as follows: an occlusion lock device and an elastic assembly (which may be a spring or the like) are provided in a clamp handle, the pushrod connects the occlusion lock device at the proximal end of the clamp handle and the elastic assembly at the distal end of the clamp handle. An inner axis and an inner groove are comprised in the clamp body, each of which is connected to one clamp jaw. In this embodiment, the motion of the pushrod can push the inner axis to move inside the inner groove, thereby pushing the proximal-side clamp jaw to slide towards the fixed distal-side clamp jaw (in another embodiment, the proximal-side clamp jaw may be fixed, so the inner groove may be pulled to move, thereby pulling the distal-side clamp jaw to slide towards the fixed proximal-side clamp jaw, or clamp jaws on both sides are both able to slide. The following description also includes embodiments where a distal-side clamp jaw is pulled to move and embodiment where clamp jaws on both sides both slide, unless otherwise stated). After the pushrod moves a certain distance inside the clamp handle, the occlusion lock device locks the pushrod to keep it still, thus fixing the distance between the distal-side clamp jaw and the proximal-side clamp jaw. When the locked occlusion lock device is unlocked, the elastic assembly restores the pushrod to its original position by elastic restoring force, thus dividing the distal-side clamp jaw and proximal-side clamp jaw. In this embodiment, the moving distance of the pushrod may be set with various predetermined distances by the occlusion lock device (i.e., once the pushrod moves a predetermined distance, the occlusion lock device automatically locks), so as to be adapted to different thicknesses of ablation tissue. In addition, as follows, the moving distance may also be predetermined in such a way so as to prevent needle heads extending out of the proximal-side clamp jaw and the distal-side clamp jaw from touching one another or to prevent the fence on clamp jaws on both sides from touching each other. The moving distance of the pushrod may also be controlled manually by operators.

Method of moving and occluding clamp jaws on both sides may also be achieved by methods other than the above ones, for example, two inner axes are provided inside the clamp body, the two inner axes being connected to the two clamp jaws, respectively, and the two clamp jaws are caused to move relative to each other with the pushrod for different spacing. Alternatively, one inner axis is provided inside the clamp body, to which two clamp jaws are both connected, and the two clamp jaws are caused to move with the pushrod for a certain relative distance, etc. The clamp handle may also be provided with no occlusion lock device or elastic assembly, and it is left to manual work to push two clamp jaws to move and fix the two clamp jaws at a certain relative distance.

In the above embodiments, the occlusion lock device may be various occlusion lock components, assemblies or structures known to those skilled in the art, for example, a snap-fit assembly, gear lock mechanism, etc. The choice of the occlusion lock device is not limited as long as it is able to lock the position and movement of the pushrod.

As a preferred embodiment of the present invention, the angle between the clamp head and the clamp body of the chemical ablation apparatus according to the present invention can be adjusted, so as to allow clamp jaws to clamp target ablation tissue at preferred angles when they are operated in a body, thus forming a preferred ablation line. For example, the clamp head may be connected to the clamp body by a rotatable damping component, which is able to rotate under the effect of external force and keep a certain angle between the clamp head and the clamp body, and the damping of the damping rotatable component keeps the angle unchanged during clipping and ablating of the chemical ablation apparatus according to the present invention. For example, the damping rotatable component may be a damping spindle. Or the clamp head is connected to the clamp body by a rotatable component with a transmission device, and the transmission device is able to control motion of the rotatable component under the effect of external force and keep a certain angle between the clamp head and the clamp body, which remains unchanged during clipping and ablating of the chemical ablation apparatus according to the present invention. For example, the rotatable component may be a hinge, and the transmission device may be a traction cable, traction threaded rod, etc.

The angle between the clamp head and the clamp body of the chemical ablation apparatus according to the present invention may be 0-180°, preferably 110-150° (namely the angle between the line starting at the joint between the clamp head and the clamp body and ending at the most distal end of the clamp head and the longitudinal axis of the clamp body).

The pipeline components of the chemical ablation apparatus according to the present invention comprise ablation reagent transporting pipelines that are in fluid communication with the needle head assembly so as to transport ablation reagent. The ablation reagent transporting pipelines connect the ablation reagent injection head and the ablation reagent supply device. The ablation reagent transporting pipelines comprise a first pipeline and a second pipeline, the first pipeline extends to the proximal-side clamp jaw, and the first pipeline connects the ablation reagent supply device at its proximal end and reaches at the distal end of the proximal-side clamp jaw at its distal end; the second pipeline extends to the distal-side clamp jaw, and the second pipeline connects the ablation reagent supply device at its proximal end and reaches at the distal end of the distal-side clamp jaw at its distal end.

In one preferred embodiment, the first pipeline and the second pipeline converge into a main pipeline inside the clamp handle, and the main pipeline goes through the clamp handle and connects the ablation reagent supply device inside or outside the clamp handle. The first pipeline and the second pipeline may also connect different ablation reagent supply devices separately inside or outside the clamp handle, thus providing the same or different chemical ablation reagents at different flow rates and pressures.

In another preferred embodiment, chemical ablation reagents of different categories or dosage are led to the first pipeline and the second pipeline, so as to achieve different ablation effects on different parts.

In the chemical ablation apparatus according to the present invention, the first pipeline and the second pipeline may be made of materials with proper chemical resistance or corrosion resistance that is capable of withstanding chemical ablation reagents. The material should be flexible and stiff to a certain degree so as to give a certain degree of flexibility to the pipelines it produces, allowing the pipelines to bend, curve and move within the ablation apparatus, and at the same time giving a certain degree of stiffness to the pipelines, allowing the pipelines to withstand pressing from other metal or rigid components within the ablation apparatus without collapse, thus avoiding uneven pressure in the pipelines as a result of obstructed flow of liquid in the pipelines, and the obstructed, insufficient fluid discharge from the needle heads, or uneven fluid discharge from each needle as a result of uneven pressure in the pipelines. Preferably, for the purpose of repeated use, materials of pipelines should be long-term durable. Optimally, though the said pipeline materials do not touch human body directly, biocompatible material is a preferred choice. The pipeline materials proper for the present invention may be selected from polyvinyl chloride, polyurethane, polyethylene, acrylonitrile-styrene-butadiene copolymer (ABS), etc., and the selection thereof is not limited as long as it can meet the above requirements. Those skilled in the art may select proper materials for the manufacture of the pipelines according to the present invention based on other common knowledge in fields of chemistry and medical materials.

In one preferred embodiment, the ablation reagent transporting pipelines gradually expand in shape at the side where an ablation injection head is connected, so as to minimize pressure difference among each needle head when supplying ablation reagents to each needle head, thus supplying ablation reagents to each needle head evenly. In order to further reduce pressure difference among each needle head, a distributing device may also be provided in the expanding part of the pipelines, such as a distributing board.

In another preferred embodiment, each of the needle heads has an independent pipeline at least on the side of the ablation reagent transporting pipelines that is close to the needle head, each pipeline supplies to one or more needle heads separately to reduce pressure difference among each needle head, and it is optional to supply ablation reagents of different dosages or categories to different needle heads, it is also optional to supply or not to supply ablation reagents to different needle heads.

In a body, there are many organs around a heart, and the outer surface of a heart is attached to the pericardium. In actual operation, when an ablation apparatus is placed and clamped on a target ablation site, needle heads on the ablation apparatus may damage surrounding tissue, such as atrial or pulmonary vein walls, causing bleeding. Therefore, needle heads of the chemical ablation apparatus of the present invention can be preferably designed to be stretchable. When the chemical ablation apparatus is put into a body, placed and clamped on target ablation tissue, needle heads are inside clamp jaws; after the ablation tissue is firmly clamped, needle heads can be controlled to extend, penetrate into target cardiac muscle tissue, and release chemical ablation medium. Extending and retracting of needle heads can be achieved by multiple methods including, but not limited to, air pressure control, hydraulic pressure control, electronic machinery control.

As a preferred embodiment of the chemical ablation apparatus according to the present invention, the needle head extension and retraction control assembly of the chemical ablation apparatus according to the present invention controls the needle heads extending out of or retracting into the clamp jaws by air pressure or hydraulic pressure. The needle head extension and retraction control assembly comprises an air bag or a liquid bag arranged on the side of the ablation reagent injection head that is away from the injection needle holes, and an elastic component is arranged between the ablation reagent injection head and the injection needle holes; the volume of the air bag or liquid bag changes by charging and discharging air or liquid, driving the ablation reagent injection head to move towards or away from the injection needle holes; the elasticity of the elastic component tends to drive the ablation reagent injection head to move away from the injection needle holes. For example, an air bag may be arranged on the side of the ablation reagent injection head inside a clamp jaw that is away from the injection needle holes, and one or more elastic components may be arranged between the ablation reagent injection head and the injection needle holes, the air bag is connected to a valve outside the chemical ablation apparatus by an air supply pipe, the valve connects an air supply device such as rubber balls, the pipeline components and the needle head assembly are placed between the air bag and the elastic component(s). When the valve is opened, air in the air bag is deflated, and pressure in the air bag decreases, volume of the air bag reduces, the elastic assembly presses the needle heads back into clamp jaws by elastic restoring force; when the valve is closed and the air bag is inflated, the air bag increases in volume, as pressure of air in the air bag exceeds elastic restoring force of the elastic assembly, the ablation reagent injection head can be pushed forward until the needle heads extend out of clamp jaws and penetrate into cardiac muscle tissue with a certain length. Controlling needle heads' extension and retraction by hydraulic pressure device may be similar to the above air pressure control, hydraulic pressure control can be achieved by replacing air bag with liquid bag, air supply pipeline with liquid supply pipeline, air supply device with liquid supply device. The length of needle heads extending out of clamp jaws can be controlled by amount of air inflated into the air bag/amount of liquid filled into the liquid bag or the length of needle heads.

As another preferred embodiment of the chemical ablation apparatus according to the present invention, the needle head extension and retraction control assembly of the chemical ablation apparatus according to the present invention controls the needle heads' extending out of or retracting into clamp jaws by electronic machinery. For example, the needle head extension and retraction control assembly comprises an electromagnetic elastic component arranged between the ablation reagent injection head and the injection needle holes, such as an electromagnetic spring, the electromagnetic elastic component is connected to an electronic control device by a wire, and the length of the electromagnetic elastic component is controlled by electric current so as to drive the ablation reagent injection head to move towards or away from the injection needle holes. For example, when the electromagnetic elastic component is not energized, elastic restoring force of the electromagnetic spring presses needle heads into clamp jaws; when the electromagnetic elastic component is energized, the electromagnetic elastic component contracts and generates an inward pull that drives the ablation reagent injection head to move towards the injection needle holes until the needle heads extend out of clamp jaws and penetrate into cardiac muscle tissue with a certain length. The length of the needle heads extending out of clamp jaws can be controlled by current intensity, or the length of the needle heads.

As another preferred method of exploitation of electronic machinery control, the needle head extension and retraction control assembly of the chemical ablation apparatus according to the present invention comprises an electronic motor arranged in the clamp jaws, the electronic motor drives the ablation reagent injection head to move towards or away from the injection needle holes by a transmission device such as threaded rod or gear. For example, the electric motor is provided on one side wall of the clamp jaw adjacent to the inner side of the clamp jaw (i.e., the side of the clamp jaw where the injection needle holes are located), which is connected to an electronic control device by a wire. A gear is installed on the electric motor, and a gear rack that engages with the gear on the electric motor is arranged on one side of the ablation reagent injection head close to the electric motor. When the electric motor rotates in one direction, the gear drives the ablation reagent injection head to move away from the injection needle holes by engaging with the gear rack, such that the needle heads retract into the clamp jaw; when the electric motor rotates in an opposite direction, the gear drives the ablation reagent injection head to move towards the injection needle holes by engaging with the gear rack until the needle heads extend out of the clamp jaw and penetrate into cardiac muscle tissue with a certain length. The length of the needle heads extending out of the clamp jaw can be controlled by running time of the electric motor, the length of the gear rack, or the length of the needle heads. Or, a gear rack is provided on one side wall of the clamp jaw adjacent to the inner side of the clamp jaw (i.e., the side of the clamp jaw where injection needle holes are located), and an electric motor with a gear that engages with the gear rack is installed on one side of the ablation reagent injection head that is close to the gear rack. Extension and retraction of needle heads can also be achieved by the same operation as that of the above embodiment.

As another preferred embodiment of electronic machinery control, a linear stepper electric motor is provided on one side of the ablation reagent injection head close to the side wall of the clamp jaw, which is connected to an electronic control device by a wire. A threaded rod of the linear stepper electric motor is arranged on the side wall of the clamp jaw. When the electric motor rotates in one direction, it can drive the ablation reagent injection head to move away from the injection needle holes, such that the needle heads retract into the clamp jaw; when the electric motor rotates in an opposite direction, it can drive the ablation reagent injection head to move towards the injection needle holes until the needle heads extend out of the clamp jaw and penetrate into cardiac muscle tissue with a certain length. The length of the needle heads extending out of the clamp jaw can be controlled by running time of the electric motor, the length of the threaded rod, or the length of the needle heads. Or, a threaded rod may be provided on one side of the ablation reagent injection head close to the side wall of the clamp jaw, and the electric motor placed on the side wall of the clamp jaw, which can also achieve the control of the needle head extension and retraction.

The chemical ablation apparatus according to the present invention may apply other methods that achieve control over the needle head extension and retraction. Therefore, the above examples do not set limit on the present invention.

As another preferred embodiment of the present invention, the chemical ablation apparatus according to the present invention also comprises cushions with proper thickness arranged on the ablation clamp jaws on both sides separately, the cushions covering the injection needle holes. The thickness of the cushions is set as equal to or slightly greater than the length of injection needle heads at their full extension on ablation clamp jaws, such that when the ablation clamp jaws clip target ablation tissue and the injection needle heads fully extend out of the clamp jaws, the press from the ablation clamp jaws on both sides and tissue between the ablation clamp jaws on both sides compresses the cushions, allowing the injection needle heads to extend out of the cushions and then penetrate into target ablation tissue. And the injection needle heads in the part of the ablation clamp jaws that does not touch cardiac muscle tissue remain inside the cushions. Under this condition, chemical ablation reagent leak is avoided along with surrounding tissue damage caused thereby when a chemical ablation reagent is injected.

Where injection needle heads in the ablation clamp jaws are not stretchable, i.e., the chemical ablation apparatus according to the present invention does not have the above needle head extension and retraction control assembly, surrounding tissue damage caused by injection needle heads on the ablation clamps can be avoided according to the present invention by arranging compressible and restorable cushions on clamp jaws on both sides. At this point, the cushions encase injection needle heads on the ablation clamp jaws completely. The thickness of the cushions is set as equal to or slightly greater than the length of injection needle heads, such that when the ablation clamp jaws are not clipping, the cushions remain in their original state with injection needle heads inside it, so when the ablation clamp is operated, the ablation clamp jaws move inside a body without causing surrounding tissue to be punctured by injection needle heads; and when the ablation clamp jaws are placed at target ablation tissue and then clip, the press from the ablation clamp jaws on both sides and tissue between the ablation clamp jaws on both sides compresses the cushions, allowing injection needle heads to extend out of the cushions and then penetrate into target ablation tissue. And injection needle heads in the part of the ablation clamp jaws that do not touch cardiac muscle tissue remain inside the cushions. Under this condition, when a chemical ablation reagent is injected, needle heads penetrating into target ablation tissue can release the chemical ablation reagent and the rest of the injection needle heads cannot release the chemical ablation reagent because they are still inside the cushion. Thus, the following situation can be avoided: needle heads on both sides of the ablation clamp head that do not penetrate into cardiac muscle tissue are exposed in pericardium or mediastinum lacuna, where the pressure is relatively low when a chemical ablation reagent is being injected, as a result, part of the chemical ablation reagent leaks, the release amount of the chemical reagent at target ablation area reduces, and surrounding tissue is damaged. When the ablation is finished, the clamp jaws on both sides release, the cushions restore to their original state for lack of press from the clamp jaws on both sides and cardiac muscle tissue, injection needle heads are encased inside the cushions, when the ablation clamp is operated, the ablation clamp jaws move in a body and do not puncture surrounding tissue with injection needle heads.

The material of the cushion should be non-toxic and chemically inert, nonpathogenic, and should not damage surrounding tissue, nor cause allergy, and have some other characteristics. Therefore, the material of the cushion may be selected from purified natural rubber, silicone rubber, polyurethane and other materials with the above characteristics.

In the chemical ablation apparatus according to the present invention, needle heads extending out of the proximal-side clamp jaw and the distal-side clamp jaw, on their sagittal planes, are at an angle of 30-150° with axes of the first pipeline and the second pipeline separately, and preferably at an angle of 90° (i.e., perpendicular).

In one embodiment, needle heads extending out of the proximal-side clamp jaw, on their sagittal plane, are at an angle of 30-90° with the axis of the first pipeline, and needle heads extending out of the distal-side clamp jaw, on their sagittal plane, are at an angle of 90-150° with the axis of the second pipeline; or needle heads extending out of the distal-side clamp jaw, on their sagittal plane, are at an angle of 30-90° with the axis of the second pipeline, and needle heads extending out of the proximal-side clamp jaw, on their sagittal plane, are at an angle of 90-150° with the axis of the first pipeline.

The size and shape of hearts of different people are slightly different, and the target ablation lines for treating different types of arrhythmias are different. Ablation devices of one specification with the same number of needle heads, the same row length, and the same row density will lead to the following results: a limited length of the needle row may cause that part of target ablation tissue is not penetrated by any needle head and not reached by any chemical ablation reagent, thus leaving a "gap"; or the excessively long row of needle heads exposes some tissues that do not need to be ablated to chemical ablation reagents, causing tissue necrosis; or the excessively long row of needle heads exposes part of needle heads out of cardiac muscle tissue and in pericardium, and under this condition, when chemical ablation reagents are injected into pipeline components, the pressure at the needle heads outside cardiac muscle tissue is relatively low, causing some chemical ablation reagents to be discharged from these needle heads, affecting the ablation effect, and the discharged chemical ablation reagent may cause damage to the surrounding tissue. Therefore, needle heads in the ablation clamp can be set with needle caps or can be set to be detachable. Imaging or 3-dimensional reconstruction of pulmonary veins and atrial tissue requiring ablation may be performed by left atrium and pulmonary vein enhanced CT or other imaging techniques before operation. The perimeter of the pulmonary vein antrum in the cross section of the sagittal plane may be measured and calculated by computerized data processing software or other measurement methods, thereby obtaining the approximate length of the pulmonary vein antrum after it is clipped, so as to further determine the row length and the number of needle heads. According to the pre-measured length, the needless injection needle heads are enclosed by needle caps. The length can also be accurately measured and calculated by pre-clipping during operation, where needle heads remain inside the clamp jaws. The length of tissue in need of ablation and necessary length of needle heads are measured by the scale on the clamp jaws and the clamp handle respectively. Or, after the pre-clipping, length range of tissue in need of ablation may be determined according to the range of electrical signal sent back by the mapping electrodes on the clamp jaws that are attached to cardiac muscle tissue.

In another preferred embodiment, needle heads of the chemical ablation apparatus according to the present invention may be set as detachable. After the length to be clipped is determined, one or more rows of needle heads are installed within the corresponding length according to the determined length, and needle heads of different lengths may be installed based on the thickness of cardiac muscle tissue in need of ablation. So, the ablation injection head may be provided with one or more rows of needle fixing holes, the needle fixing holes are in parallel with and correspond to the injection needle holes provided on the clamp jaws. The needle fixing holes are connected to the ablation reagent transporting pipelines, and when the needle heads are not installed, the needle fixing holes are closed, preventing chemical ablation reagents from leaking, and after the needle head are installed, the needle heads connect the ablation reagent transporting pipelines. In order to ensure that the needle tips are not exposed to the outside of the clamp jaws after needle heads of different lengths are installed in the needle fixing holes, the depth of the needle fixing holes can be set to be equal to or greater than the longest preset length of needle heads, and the length at which the needle heads are installed in the needle fixing holes can be adjusted as needed. For example, a step structure with different depths is provided in the needle fixing holes, and at the rear of the needle heads is a step structure matching the shape of the step structure in the needle fixing holes, and needle heads of different length specifications are respectively fixed on steps of different depths, thus providing needle heads with different injection depths, whose tips are not exposed to the outside of the clamp jaws. Or, thread is arranged in the needle fixing holes. A thread matching the shape of the thread in the needle fixing holes is at the rear of the needle heads, and needle heads of different length specifications are screwed into the needle fixing holes, and needle heads of different injection depths may be achieved by adjusting the degree at which needle heads are screwed into needle fixing holes. Other designs may also be applied to meet this requirement. Therefore, the above examples do not set limit on the present invention.

In another preferred embodiment, the needle head of the chemical ablation apparatus according to the present invention can be configured to have an end outlet at the head end, or an end outlet at the head end and one or more side holes on its side, so as to enable more target ablated tissue to contact chemical ablation reagent.

When injection needle heads extend out of a cushion or penetrate into cardiac muscle tissue, in order to prevent the injection needle heads from being blocked by the cushion or cardiac muscle tissue, the injection needle heads may adopt the shape of conventional injection needle heads, i.e., an elongated hollow cylindricity, and needle tip at distal end is bevel with acute angle. However, unlike the conventional injection needle heads, the head end of needle tip at distal end is closed, so as to prevent the needle holes from being blocked by the cushion when the injection needle heads extend out of the cushion or by cardiac muscle tissue when the injection needle heads penetrate into cardiac muscle tissue; several side holes are opened under the head end to inject chemical ablation reagent into cardiac muscle tissue. When an ablation reagent is injected via the injection needle heads, the ablation reagent instantaneously ejecting from an end outlet at a high pressure may break through the thin cardiac muscle tissue, allowing more ablation agent into the heart chamber instead of target ablation tissue. This design of closed-end outlets at head end also helps to avoid such accidents.

The dosage of a chemical ablation reagent to be injected may be calculated by the calculation formula as follows: Total dosage of a chemical ablation reagent to be injected=threshold for reagent injection dosage of each injection needle head×number of injection needle heads, or when an injection pump is used: Time for injection of a chemical ablation reagent=(threshold for reagent injection dosage of each injection needle head×number of injection needle heads)/injection speed. The threshold for reagent injection dosage injected by each injection needle refers to a minimum or threshold enabling that: with the injection needle head as the center of a ball, the damage area (or volume) of ablated tissue caused by an injected chemical ablation reagent by the injection needle head overlaps with the damage area (or volume) caused by an adjacent injection needle head (as described above) so that no blind spot is left on the ablated tissue (i.e., no undamaged tissue is left). In practical use, reagent injection dosage of each injection needle head should be equal to or slightly greater than the threshold (generally controlled as about 10-40% greater than the threshold).

In order to verify whether an ablation line is continuous and complete and whether a gap is left after an ablation is finished, the chemical ablation apparatus according to the present invention also comprises an electrocardiographic mapping component, by which the conduction condition of electrocardiosignals and/or external electrical stimulus signals around the target ablation tissue is detected, thus determining the ablation effect (or effect of the ablation). The electrocardiographic mapping component comprises mapping electrodes and a wire that connects the mapping electrodes to an electrocardiographic measurement device, which detects the conduction condition of electrocardiosignals and/or external electrical stimulus signals around the target ablation tissue. The mapping electrodes are arranged on the clamp jaws and are close to the injection needle holes, for example, outside the injection needle holes or to both sides of the injection needle holes (the electrodes are arranged on a cushion if there is any on the clamp jaws, and then when the injection needle heads penetrate out of the cushion, the electrodes are close to the needle heads, for example, the electrode is outside the injection needle heads or to both sides of the injection needle heads, and is arranged in parallel with the injection needle heads). The electrocardiographic measurement device may include a processor, a display, a polygraph, a stimulator, etc.; the processor may be located inside or outside the chemical ablation apparatus, which is connected to the chemical ablation apparatus by a wire; the display may be placed on the chemical ablation apparatus (surface) or outside the chemical ablation apparatus, which is connected to the chemical ablation apparatus by a wire; the polygraph and stimulator can be placed outside the chemical ablation apparatus, and are connected to the chemical ablation apparatus by a wire.

In one preferred embodiment, mapping electrodes are arranged on one side of the injection needle holes in the clamp jaws (the mapping electrodes are arranged on a cushion if there is any on the clamp jaws, and then when the injection needle heads penetrate out of the cushion, the electrodes are on one side of the injection needle heads). A plurality of mapping electrodes are arranged with equal spacing, preferably in parallel with the injection needle holes. The mapping electrodes connect a wire. The wire is arranged inside the chemical ablation apparatus, connecting the mapping electrodes at one end and a processor at the other end. The processor is placed inside or outside the chemical ablation apparatus and connects a display. When the clamp head clips target ablation tissue, mapping electrodes on the clamp jaws attach to epicardium next to target ablation tissue, thus conducting electrocardiosignal to the processor through the wire. The processor may perform simple calculation by a preset program to verify whether the ablation line is complete, and whether there is a "gap" and its location. The electrocardiosignal of target ablation tissue is displayed on the display in real time to show whether the ablation is complete.

In another preferred embodiment, mapping electrodes are arranged to both sides of the injection needle holes in the clamp jaws (the mapping electrodes are arranged on a cushion if there is any on the clamp jaws, and then when the injection needle heads penetrate out of the cushion, the electrodes are to both sides of the injection needle heads). A plurality of mapping electrodes are arranged with equal spacing, preferably in parallel with the injection needle holes. The mapping electrodes connect a wire. The wire is arranged inside the chemical ablation apparatus, connecting the mapping electrodes at one end and a processor at the other end. The processor is placed inside or outside the ablation apparatus and connects a display. The electrocardiographic mapping system may also connect a stimulator externally. When the clamp head clips target ablation tissue, mapping electrodes on the clamp jaws attach to epicardium next to target ablation tissue, thus conducting electrocardiosignal to the processor through the wire. The processor may perform simple calculation by a preset program to verify whether the ablation line is complete, and whether there is a "gap" and its location. The electrocardiosignal of target ablation tissue is displayed on the display in real time to show whether the ablation is complete. It is also optional that the mapping electrodes on both sides of the clamp jaws release electrical stimulus signals separately by the stimulator that is externally connected to the electrocardiographic mapping system. The mapping can verify whether the electrical stimulus signals can be conducted through target ablation tissue with the mapping electrodes on the other side, whether the ablation line is complete, whether there is a "gap" and whether bidirectional block is achieved at target ablation tissue, so as to determine the ablation result and necessity of another ablation.

As a preferred embodiment, the chemical ablation apparatus according to the present invention also comprises a pulley, around which the pipeline components and/or the wire are wound, the pipelines and/or the wire's extension or retraction in the clamp body is adjusted by decreasing or increasing the number of times of winding the pipeline components and/or the wire to adapt to the motion of the clamp head. The pulley in this embodiment may be placed inside the clamp handle or outside the clamp jaws.

The chemical ablation apparatus according to the present invention may also comprise a fence. The fence is located on both sides of the needle holes in the proximal-side clamp jaw and the distal-side clamp jaw, and also at the end of the distal end of the clamp jaws and extending towards the tip end of the needle heads. The height of the fence is set as slightly greater or slightly smaller than or equal to the length of the needle heads in the lengthwise direction of the needle heads, such that when the clamp jaws on both sides come close, the needle heads extending out of them won't touch one another, thereby avoiding damage. And when the clamp jaws on both sides clip, the fence can fix target ablation cardiac muscle tissue, and make the target ablation cardiac muscle tissue inside the fence on two both sides project towards the clamp jaws slightly, enabling needle heads to penetrate into target ablation cardiac muscle tissue more easily.

The chemical ablation apparatus according to the present invention achieves continuous, complete ablation line and transmural damage by the method of chemical ablation, and it can also be used to ablate ventricular arrhythmia; needle heads may extend out of or retract into clamp jaws in order not to damage issue; needle heads on clamp jaws are detachable to allow for individual treatment for different patients with different ablation position; cushions are arranged on clamp jaws to prevent needle heads from damaging tissue and chemical ablation reagents from leaking via needle heads that are outside target ablation tissue, which impairs ablation effect and damages surrounding tissue; and after an ablation, whether a "gap" is in an ablation line that can still conduct electricity can be mapped to verify the ablation effect. If a "gap" exists, supplementary ablation may be performed during the operation in time, thus reducing recurrence rate of arrhythmia. And cost of the ablation apparatus, ancillary equipment together with expense of arrhythmia surgical operation is reduced. The technical threshold for arrhythmia surgical treatment is lowered, allowing more hospitals to be able to perform this treatment.

DESCRIPTION OF THE DRAWINGS

FIG. 14 illustrates injection needle holes arranged in a single row.

FIG. 15 illustrates injection needle holes arranged in two staggered rows.

FIG. 16 illustrates injection needle holes arranged in three staggered rows.

FIG. 17 illustrates an electrocardiogramafore an ablation.

FIG. 18 illustrates an electrocardiogramg an ablation.

FIG. 19 illustrates an electrocardiogramafter an ablation, where a distal-side electrode is able to map electrical stimulus released from a proximal-side electrode, indicating a "gap" may be left.

FIG. 20 illustrates an electrocardiogramafter an ablation, where a proximal-side electrode is able to map electrical stimulus released from a distal-side electrode, indicating a "gap" may be left.

FIG. 21 illustrates an electrocardiogramafter an ablation, where a distal-side electrode does not map electrical stimulus released from a proximal-side electrode, indicating a complete and continuous ablation line and a successful ablation.

FIG. 22 illustrates an electrocardiogramafter an ablation, where a proximal-side electrode does not map electrical stimulus released from a distal-side electrode, indicating a complete and continuous ablation line and a successful ablation.

FIG. 23 illustrates an electrocardiogram successful ablation.

EMBODIMENT

Definition

Distal side: in this description, when "distal side" is mentioned to describe the apparatus according to the present invention, it means the side that is relatively far from a user.

Proximal side: in this description, when "proximal side" is mentioned to describe the apparatus according to the present invention, it means the side that is relatively close to a user.

Distal end: in this description, when "distal end" is mentioned to describe the apparatus according to the present invention, it means the end that is relatively far from a user or the main body (e.g., clamp handle or clamp body) of the apparatus according to the present invention.

Proximal end: in this description, when "proximal end" is mentioned to describe the apparatus according to the present invention, it means the end that is relatively close to a user or the main body (e.g., clamp handle or clamp body) of the apparatus according to the present invention.

Sagittal plane: a sagittal plane refers to the plane that goes through the vertical axis and the longitudinal axis of a human body (or other objects), i.e., mid-sagittal plane, and all planes parallel to it, i.e., a sagittal plane divides a human body or an object into left and right halves.

Coronal plane: a coronal plane refers to a plane that goes through the vertical axis and the horizontal axis of a human body (or other objects) and all planes parallel to the plane, i.e., a coronal plane divides a human body or an object into front and back halves.

A chemical ablation reagent: various chemical reagents or a combination of reagents which can cause coagulative necrosis to cardiac muscle tissue, such as anhydrous ethanol, anhydrous propanol, glycerol, iopromide mixture, or mixture thereof.

A threshold for reagent injection dosage injected by each needle head: minimum or threshold enabling that: with the needle head as the center of a ball, the damage area (or volume) of ablated tissue caused by an injected chemical ablation reagent by the needle head overlaps with the damage area (or volume) caused by an adjacent needle head (as described above) so that no blind spot is left on the ablated tissue (i.e., no undamaged tissue is left).

Figure 1:
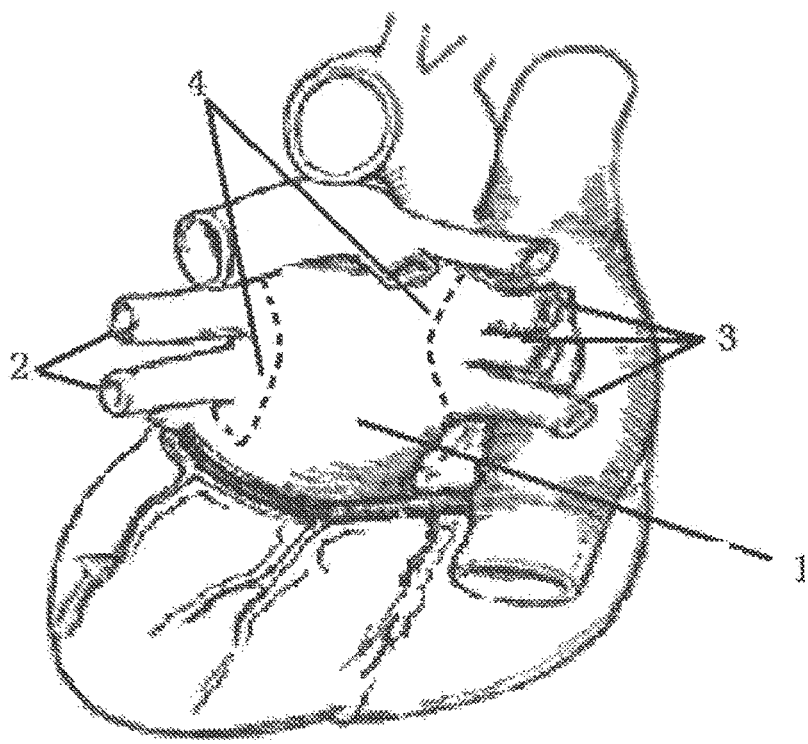
FIG. 1 is a schematic view of a pulmonary vein and its surrounding atrial tissue.

Pulmonary vein antrum: the joint between the pulmonary vein and left atrium, please refer to reference sign 4 in FIG. 1.

Preferred embodiments of the present invention are described with reference to the drawings next. It is to be understood by those skilled in the art that the embodiments or examples described in the following part with reference to the drawings are only for explaining the optimal embodiment of the present invention, not to limit the scope of the present invention within these embodiments. Various improvements and changes may be made to the present invention based on the following embodiments. And all of these improvements and changes are within the scope of the present invention.

FIG. 1 is a back view of a heart, wherein 1 is left atrium, 2 is left pulmonary vein, 3 is right pulmonary vein, 4 is Pulmonary vein antra on either side, the part that is clamped by the clamp head of the chemical ablation apparatus according to the present invention and is injected with chemical ablation reagents by the clamp head of the chemical ablation apparatus according to the present invention.

Figure 2:
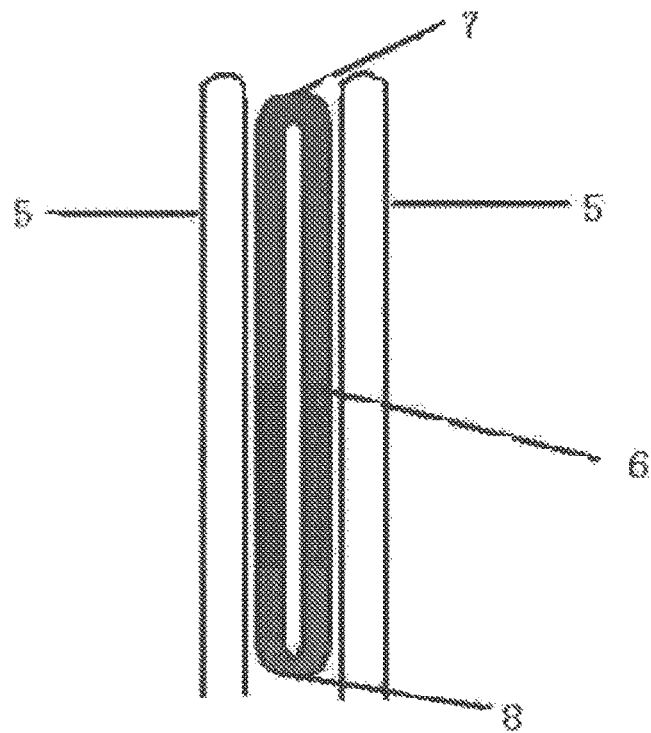
FIG. 2 is a schematic view of a "gap" in a pulmonary vein when it is clipped by one current radiofrequency ablation clamp.
Figure 4:
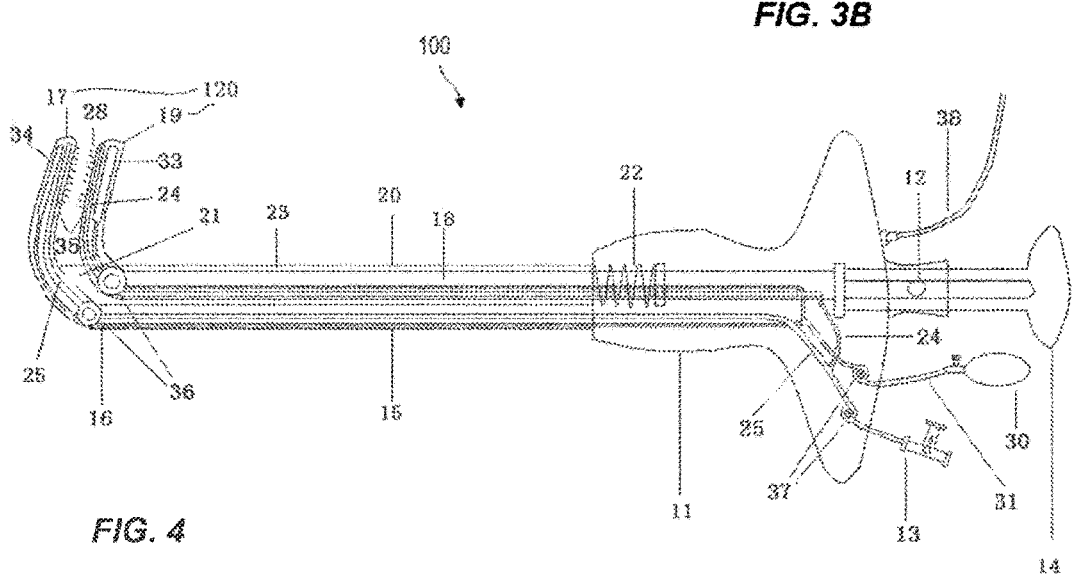
FIG. 4 is a cross-sectional view of a chemical ablation apparatus in one embodiment of the present invention.

FIG. 2 presents a schematic view of cross section of a sagittal plane of a pulmonary vein antrum after it is clamped by an ablation apparatus, wherein 5 is clamp jaws on both sides, 6 is a cross section of a sagittal plane of the pulmonary vein antrum, 7 is the part of the pulmonary vein antrum between the distal ends (or top ends) of the two clamp jaws that does not touch the clamp jaws, 8 is the part of the pulmonary vein antrum between the proximal ends (or bottom) of the two clamp jaws that does not touch the clamp jaws. When using a traditional bipolar radiofrequency ablation clamp, coagulative necrosis of atrial tissue cannot be caused in 7 and 8 because atrial tissue in 7 and 8 cannot reach the ablation electrodes on clamp jaws, leaving isolation "gap" in pulmonary veins which may lead to postoperative atrial arrhythmia. However, with the chemical ablation apparatus according to the present invention, needle heads 28 (as shown in FIG. 4) provided on clamp jaws of the ablation apparatus may penetrate into pulmonary vein antrum tissue. Therefore, even if clamp jaws cannot reach the cardiac muscle tissue in 7 and 8, needle heads 28 are able to reach these two parts. And an injection of chemical ablation reagents by needle heads 28 can cause approximately spherical coagulative necrosis inside the tissue. Complete circumferential pulmonary vein isolation can be achieved and "gap" can be avoided by adjusting space between needle heads 28 and dosage of injected chemical ablation reagents.

Figure 3A:
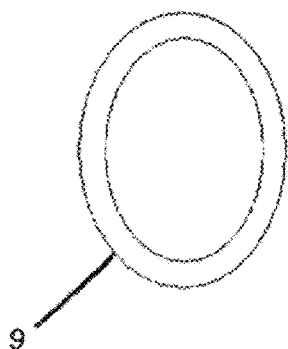
FIGS. 3a and 3b are schematic views of length change in a pulmonary vein before and after it is clipped, respectively.
Figure 3B:
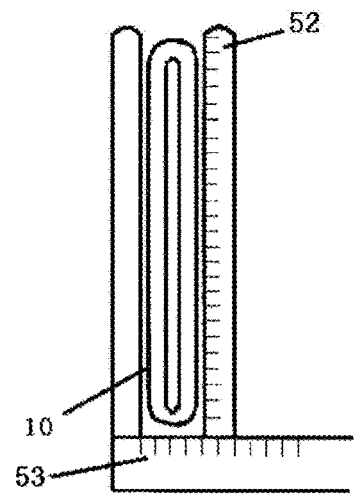
Figure 9:
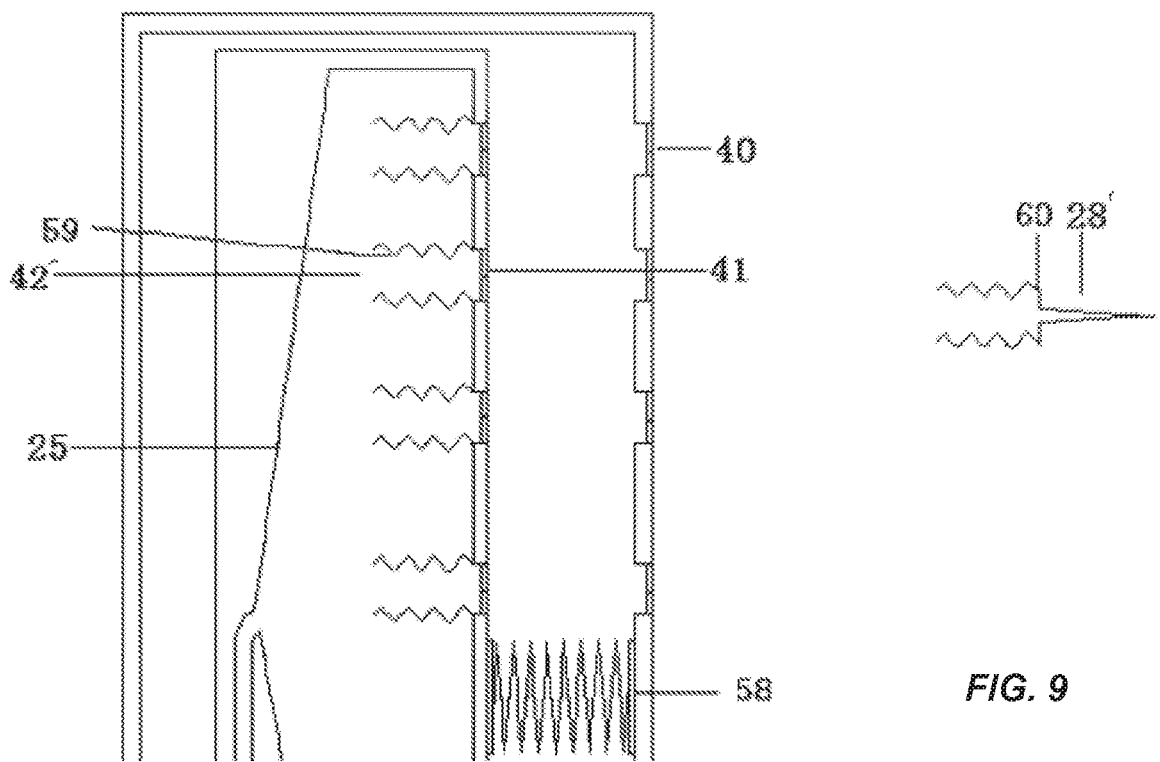
FIG. 9 is a partial enlarged view of a sagittal plane of a distal-side clamp jaw of the chemical ablation apparatus in one embodiment for the present invention.

In FIGS. 3a and 3b, 9 is a schematic view of cross section of a sagittal plane of pulmonary vein antrum under natural condition, 10 is a schematic view of cross section of a sagittal plane of pulmonary vein antrum after it is clamped by the ablation apparatus, showing that after the pulmonary vein antrum is clamped, its form changes while its perimeter in cross section of sagittal plane remains unchanged. Therefore, in order to achieve better ablation effects and reduce the occurrence rate of a "gap", imaging or 3-dimensional reconstruction of pulmonary veins and atrial tissue requiring ablation may be performed by left atrium and pulmonary vein enhanced CT or other imaging techniques before operation. The perimeter of the pulmonary vein antrum in the cross section of the sagittal plane may be measured and calculated by computerized data processing software or other measurement methods, thereby obtaining the approximate length of the pulmonary vein antrum after it is clipped. In addition, the length can also be accurately measured and calculated by pre-clipping during operation, where a graduated ablation apparatus without any needle head or with needle heads retracted inside clamp jaws may be employed to ascertain the accurate length requiring clipping. As shown in the figure, after the pulmonary vein antrum is clipped by clamp jaws, the length of the pulmonary vein antrum after it is clipped is measured by using a first scale 52 on the clamp jaw so as to obtain the row length of necessary needle heads; the thickness of the pulmonary vein antrum after it is clipped is measured by using a second scale 53 on the clamp handle so as to obtain the necessary penetration depth of injection needle heads, i.e., the necessary length of needle heads. Then injection needle heads of a certain number and a certain length are configured according to the length and thickness that are projected.

FIG. 4 is a cross-sectional view of a chemical ablation apparatus 100 in one embodiment of the present invention. As shown in the figure, the chemical ablation apparatus of the present invention comprises the following: a clamp handle 11 with an occlusion lock device 12 and an ablation reagent supply device 13 on its proximal end; a pushrod 14 provided in the clamp handle 11 and extending along the axis of the clamp handle 11 inside the clamp handle 11, the pushrod 14 connecting the occlusion lock device 12 at the proximal end of the clamp handle 11 and an elastic assembly 22 at the distal end of the clamp handle 11; a clamp body 15 extending out of the distal end of the clamp handle 11, and the distal end of the clamp body 15 extends into a connector 16; a clamp head 120 comprising a distal-side clamp jaw 17 and a proximal-side clamp jaw 19, with the distal-side clamp jaw 17 connected to the distal-side end of the connector 16. The clamp body 15 comprises an inner wall 20, an inner axis 18 and an inner groove 23, wherein the inner wall 20 and the inner groove 23 form a tubular cavity where the inner axis 18 is able to reciprocate in the tubular cavity along the inner groove 23 under the effect of the pushrod 14, wherein the proximal-side end of the inner axis 18 is connected to the distal-side end of the pushrod 14 by the elastic assembly 22 and the distal-side end of the inner axis 18 protrudes out of the distal end of the clamp handle 11 when receiving no push from the pushrod 14. The connector 16 is formed by the extending a part of the clamp body 15 that forms the inner groove 23 to the distal end of the ablation apparatus, and a chute 21 is formed by extending the inner groove 23 in the connector 16; the distal-side clamp jaw 17 is arranged at the distal-side end of the connector 16 and is arc-shaped; the proximal-side clamp jaw 19 is arranged at the distal-side end of the inner axis 18 and is arc-shaped, and the proximal-side clamp jaw 19 is able to slide toward the distal-side clamp jaw 17 along the chute 21 by the motion of the inner axis under the effect of the pushrod 14; a first pipeline 24 extends and successively goes through the clamp handle 11, the pushrod 14, the inner axis 18 and the proximal-side clamp jaw 19, the first pipeline 24 is connected at its proximal end to the ablation reagent supply device 13 arranged outside the clamp handle 11, while the distal end of the first pipeline 24 reaches the distal-side end of the proximal-side clamp jaw 19; a second pipeline 25 extends and successively goes through the clamp handle 11, the clamp body 15 and the distal-side clamp jaw 17, and the second pipeline 25 is connected at its proximal end to the ablation reagent supply device 13 arranged outside the clamp handle 11, while the distal end of the second pipeline 25 reaches the distal-side end of the distal-side clamp jaw 17. In FIG. 4, the two pipelines converge into a main pipeline inside the proximal end of the clamp handle 11, which leads to an ablation reagent supply device. A needle head extension and retraction control system in this embodiment comprises a controlling balloon 30, an air supply pipe 31 and a needle head extension and retraction control component consisting of a proximal-side air bag 33 and a distal-side air bag 34 and an elastic component 35. A one-way valve is provided on the top of the controlling balloon 30, the proximal end of the air supply pipe 31 is connected to the one-way valve of the controlling balloon 30, the air supply pipe 31 enters into the clamp handle 11 at proximal end of the clamp handle 11, goes through the clamp handle 11, the clamp body 15, the connector 16 and reaches the proximal-side clamp jaw 19 and the distal-side clamp jaw 17, and separately connects the proximal-side air bag 33 inside the proximal-side clamp jaw and the distal-side air bag 34 inside the distal-side clamp jaw. The proximal-side air bag 33 is located outside (i.e., the proximal side of) the first pipeline 24 inside the proximal-side clamp jaw 19, and the distal-side air bag 34 is located outside (i.e., the distal side of) the second pipeline 25 inside the distal-side clamp jaw 17. Parts of the first pipeline 24, the second pipeline 25 and the air supply pipe 31 of a pipeline system that is inside the clamp handle are separately wound around a pulley 37. A rotatable damping component 36 is provided at the joint between the clamp body 15 and the connector 16. A wire 38 is arranged at the proximal end of the clamp handle 11.

Figure 5:
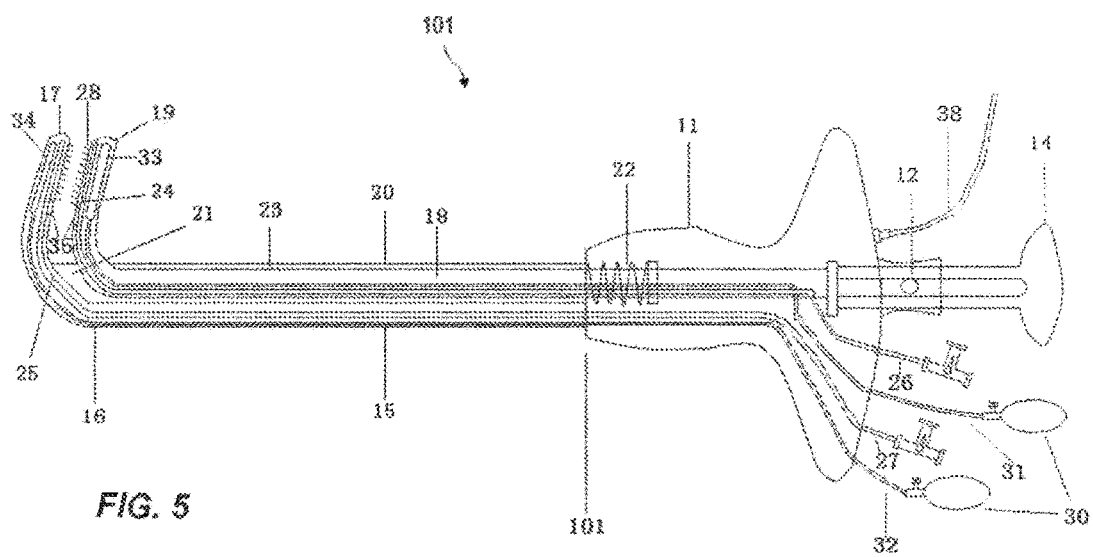
FIG. 5 is a cross-sectional view of a chemical ablation apparatus in another embodiment of the present invention.

FIG. 5 is a cross-sectional view of a chemical ablation apparatus 101 in another embodiment of the present invention. As shown in the figure, a first pipeline 24 and a second pipeline 25 in this embodiment separately extend out of a clamp handle at the proximal end of the clamp handle 11, and respectively connect two ablation reagent supply devices 26 and 27. And a proximal-side air bag 33 and a distal-side air bag 34 respectively connect a first air supply pipe 31 and a second air supply pipe 32, the proximal ends of the two air supply pipes are both connected to controlling balloons. The rest is the same as that in FIG. 4 (part of the reference numbers is not given).

In a non-working state, the two clamp jaws 17 and 19 are separate from each other; when an ablation is being performed, the chemical ablation apparatus is placed in a thorax, the positions of the connector 16 and the rotatable damping component 36 are adjusted so as to place the two clamp jaws 17 and 19 on the target ablation tissue oppositely, the pushrod 14 is pushed until the pushrod 14 triggers an occlusion lock device 12, at this time the pushrod 14, the inner axis 18 and the proximal-side clamp jaw 19 are all fixed to make sure that the two clamp jaws 17 and 19 are tightly and closely clamped on and attached to the target ablation tissue, during this process, needle heads 28 are placed inside the two clamp jaws 17 and 19 and are not outside the clamp jaws 17 and 19, so they will cause no puncture to the surrounding tissue. When the one-way valve on the controlling balloon 30 is closed, the controlling balloon 30 is used to supply air to the air supply pipe 31 as well as the proximal-side air bag 33 and the distal-side air bag 34; pressure in the two air bags is increased, when the pressure in the two air bags is higher than the elastic restoring force of the elastic component 35, the proximal-side air bag 33 pushes the ablation reagent injection head in the proximal-side clamp jaw 19 and needle heads 28 connected to the injection head, so as to make the needle heads extend out of the clamp jaw; likewise, the distal-side air bag 34 pushes the ablation reagent injection head in the distal-side clamp jaw 17 and needle heads 28 connected to the injection head, so as to push the needle heads 28 out of the clamp jaw. The needle heads 28 on the two clamp jaws 17 and 19 penetrate into the target ablation tissue without touching one another.

In the embodiment as shown in FIG. 4, a chemical ablation reagent is simultaneously injected into the two pipelines 24 and 25 through the single ablation reagent supply device 13, the reagent reaches the clamp jaws 17 and 19 through the two pipelines 24 and 25, then the reagent is injected into cardiac muscle through the needle heads 28 on the clamp jaws 17 and 19 to ablate. In the embodiment as shown in FIG. 5, two ablation reagent supply devices 26 and 27 provided in the clamp handle 11 respectively connect the first pipeline 24 and the second pipeline 25. By this design, when ablation is performed, chemical ablation reagents of the same category and dosage are able to be injected into the two pipelines 24 and 25 at the same speed and pressure, so as to achieve the same ablation effects on the cardiac muscle tissue penetrated by the needle heads 28 on the two clamp jaws 17 and 19. As shown in FIG. 5, chemical ablation reagents of different categories and dosages are able to be injected into the two pipelines 24 and 25 at different speeds and pressures as needed, so as to achieve different ablation effects on the cardiac muscle tissue penetrated by the needle heads 28 on the two clamp jaws 17 and 19. It is also an option to extend needle heads on one side of the clamp jaw and not to extend needle heads on the other side of the clamp jaw as needed, so as to perform chemical ablation only to the cardiac muscle tissue on the one side where needle heads extend out of the clamp jaws.

After ablation to target tissue is finished, the one-way valve on the controlling balloon 30 is opened, air in the two air bags is discharged through the air supply pipe 31 and the one-way valve. Pressure in the two air bags decreases, when the pressure in the two air bags is lower than the elastic restoring force of the elastic component 35, the elastic component 35 pushes, in a reverse direction, the ablation reagent injection head in the two clamp jaws and the needle heads 28 connected to the injection reagent head, so as to push the needle heads 28 back into the clamp jaws. Unlocking is achieved by simply opening the occlusion lock device 12, the pushrod 14 may be pushed by the elastic assembly 22 back to its original position. As the pushrod 14, the inner axis 18 and the proximal-side clamp jaw 19 constitute an interconnecting linkage, the inner axis 18 and the proximal-side clamp jaw 19 also return to their original positions. The two clamp jaws 17 and 19 open and loosen the target ablation tissue, and the ablation is finished.

In this embodiment, parts of the first pipeline 24, the second pipeline 25 and the air supply pipe 31 of a pipeline system that is inside the clamp handle can be wound around the pulley 37 for several times, such that when the pushrod 14 pushes or pulls the inner axis 18 and the proximal-side clamp jaw 19 to make the inner axis 18 and the proximal-side clamp jaw 19 move relative to the distal-side clamp jaw 17 in the clamp handle 11 and the clamp body 15, the first pipeline 24, the second pipeline 25 and the air supply pipe 31 of the pipeline system can be maintained at adequate length and the pipeline can be prevented from obstruction caused by folds. In this embodiment, a rotatable damping component 36 is provided at the joint between the clamp body 15 and the clamp head 120, by which the angle of the clamp body 15 and the two clamp jaws 17 and 19 of the clamp head 120 is adjusted, so as to operate the clamp jaws to reach different anatomic sites and perform ablation. In this embodiment, a wire 38 is arranged at the proximal end of the clamp handle 11, which enters into the clamp handle, goes through the clamp handle 11, the clamp body 15 and the clamp head 16 and reaches at the clamp jaws 17 and 19 on two sides, and separately connects to each mapping electrode on the clamp jaws on two sides. The wire may connect, at the other end, medical facility such as a display, an electrocardiographic measurement device and a stimulator, such that mapping and stimulation of cardiac electric activities can be performed before, during and after ablation, and ablation effects can be verified. The wire can also be wound around the pulley 37.

Figure 6:
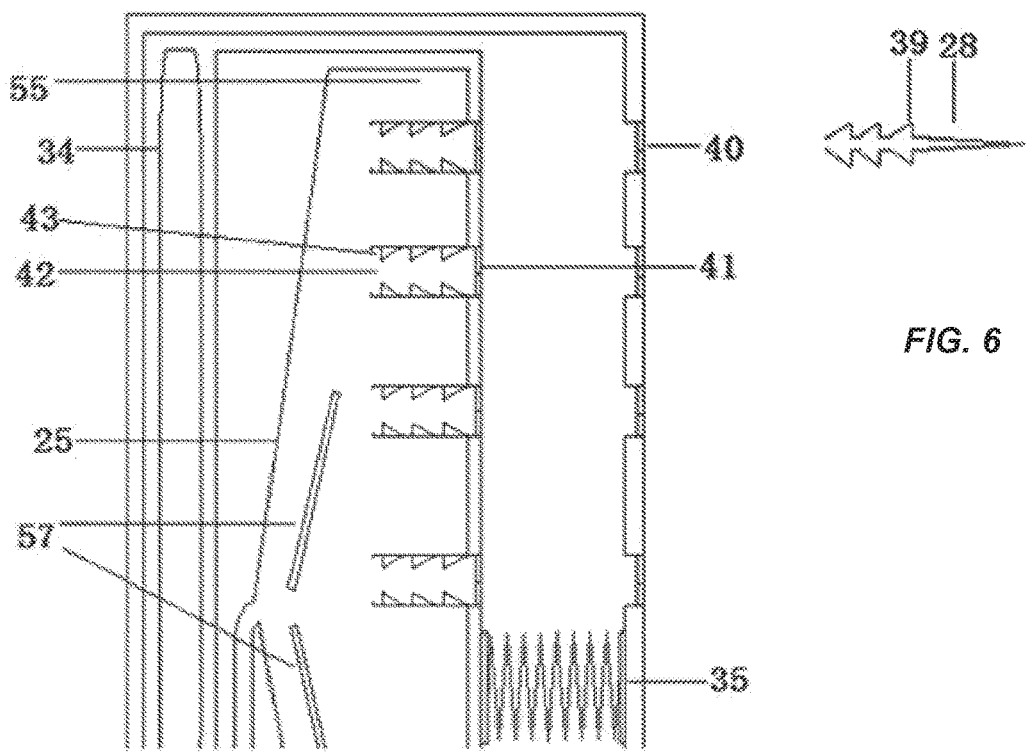
FIG. 6 is a partial enlarged view of a sagittal plane of a distal-side clamp jaw of the chemical ablation apparatus according to the present invention.

FIG. 6 is a partial enlarged view of a sagittal plane of a distal-side clamp jaw in one embodiment for the chemical ablation apparatus according to the present invention. Unless otherwise specified, the partial enlarged view of the sagittal plane of the proximal-side clamp jaw according to the present invention is the same as that in FIG. 6. Wherein the distal end of the second pipeline 25 gradually expands on the side of the clamp jaw that connecting an ablation reagent injection head 55 and connects the ablation reagent injection head 55. In order to further balance the pressure of liquids in each needle head, a distributing board 57 may be arranged at the expanded part of the second pipeline 25. Needle fixing holes 42 are provided on ablation reagent injection head 55, and a plurality of steps 43 are provided on the needle fixing holes 42. Obturators 41 for needle fixing hole is provided at the end of the needle fixing holes 42. Injection needle holes 40 are provided in the clamp jaw and is placed in parallel with and corresponding to each needle fixing hole 42, which is also arranged with obturators for injection needle hole on it. An elastic component 35 is provided between the ablation reagent injection head 55 and the inner wall of the clamp jaw on the side of the injection needle holes. An air bag 34 is provided on the outer wall of the clamp jaw on the side of the ablation reagent injection head 55 distal from the injection needle hole. As shown in the figure, needle heads 28 show the structure of needle heads in an embodiment of the chemical ablation apparatus according to the present invention; one end of a needle head 28 is a needle tip and the other a rear of needle head, with a plurality of steps 39 arranged on the rear of needle head. In this figure, no needle head 28 is provided on the injection needle holes 40 or the needle fixing holes 42, and at this point, target ablation tissue may be pre-clipped. By a first scale 52 on the clamp jaw, the length of ablation line on target ablation tissue is measured, so as to determine the length range and necessary number of needle heads to be installed. By a second scale 53 on the clamp jaw, the thickness of target ablation tissue is measured, so as to determine the necessary depth for injection needle heads to penetrate into target ablation tissue, i.e., the necessary length of injection needle heads to be installed.

Figure 7:
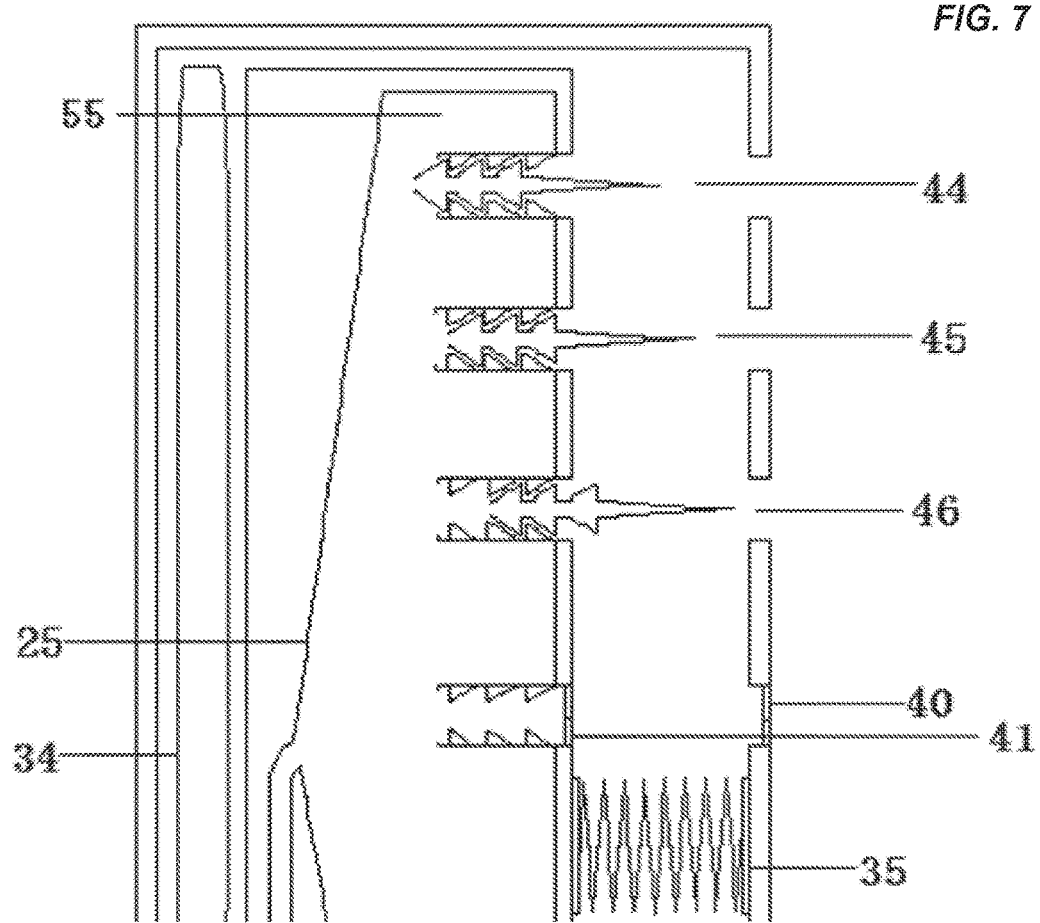
FIG. 7 is a partial enlarged view of a sagittal plane of a distal-side clamp jaw of the chemical ablation apparatus according to the present invention. In this figure, injection needle heads are installed in injection needle holes and the injection needle heads are inside clamp jaws.

FIG. 7 is a partial enlarged view of a sagittal plane of a distal-side clamp jaw in one embodiment for the chemical ablation apparatus according to the present invention. Unless otherwise specified, the partial enlarged view of the sagittal plane of the proximal-side clamp jaw according to the present invention is the same as that in FIG. 7. As shown in FIG. 7, needle heads are installed on a plurality of needle fixing holes 44, 45 and 46 as desired. The length of injection needle heads to be installed is chosen according to the thickness of tissue in need of ablation, so as to make sure that needle heads are able to penetrate into target ablation tissue at a depth that is deep enough for ablation but not deep enough to pierce target ablation tissue. As shown in the figure, in the needle fixing hole 44, steps 39 on a rear of needle head are all locked in steps 43 on the needle fixing hole, leaving minimum length of a needle tip of a needle head outside; in the needle fixing hole 45, steps 39 on a rear of needle head are partly locked in steps 43 on the needle fixing hole, leaving moderate length of a needle tip of a needle head outside; in the needle fixing hole 46, only one step 39 on a needle body of a needle head is locked in step 43 on the needle fixing hole, leaving maximum length of a needle tip of a needle head outside; the necessary length to be penetrated into target ablation tissue by a needle head can be adjusted by this way. As shown in the figure, obturators on the needle fixing holes 44, 45 and 46 in which needle heads are installed and obturators on the corresponding injection needle holes are all opened, while the obturator on the needle fixing hole 41 with no needle head installed and the obturator on its corresponding injection needle hole 40 are closed. After needle heads are installed as needed, pressure of the air bag 34 is low, elastic restoring force of the elastic component 35 is greater than the pressure of the air bag 34, making the part of the second pipeline 25 that is inside the clamp jaw attach to the outer wall of the clamp jaw. As shown in the figure, at this point, all needle tips of needle heads of different length that are installed are not exposed outside of the clamp jaw. At this moment, the clamp jaws may clip target ablation tissue again. When the clamp jaw is being placed, no puncture will be done to surrounding tissue because needle heads are inside the clamp jaw.

Figure 8:
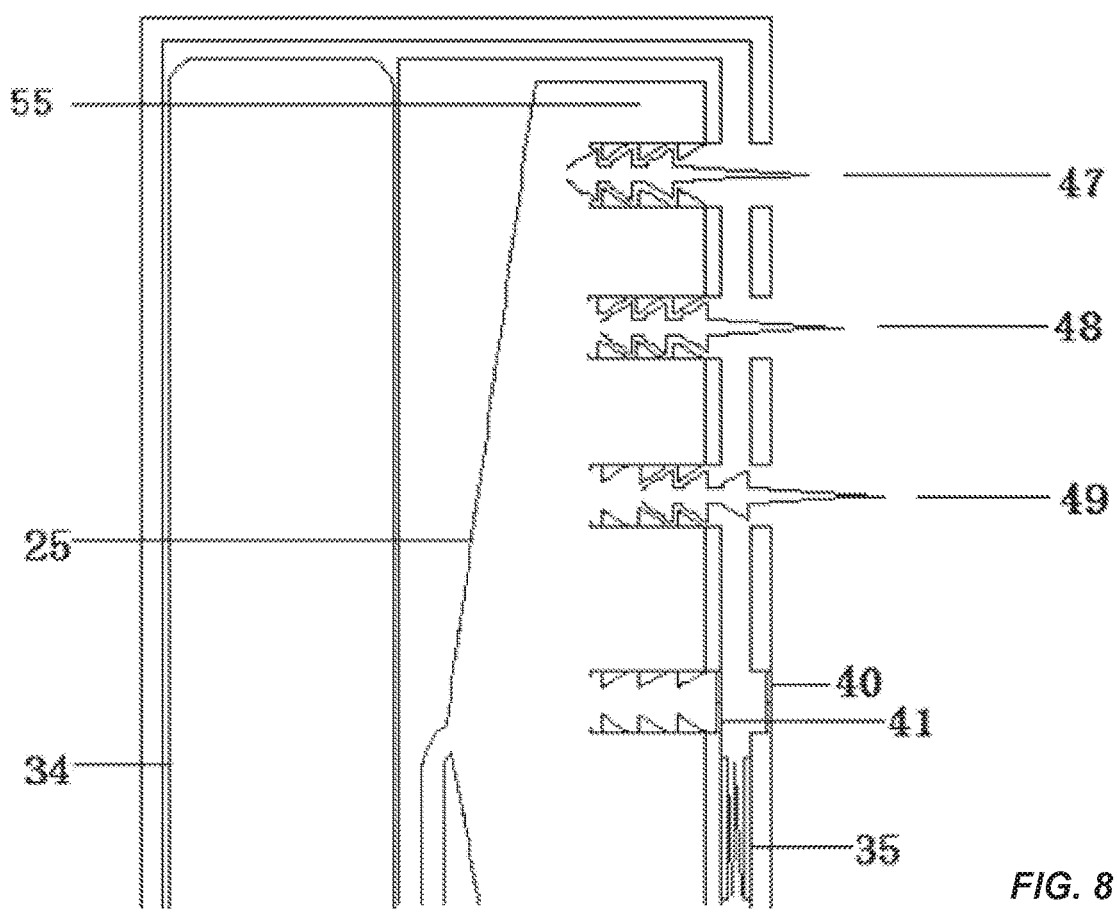
FIG. 8 is a partial enlarged view of a sagittal plane of a distal-side clamp jaw of the chemical ablation apparatus according to the present invention. In this figure, injection needle heads are installed in injection needle holes and the injection needle heads are outside clamp jaws.

FIG. 8 is a partial enlarged view of a sagittal plane of a distal-side clamp jaw in one embodiment for the chemical ablation apparatus according to the present invention. Unless otherwise specified, the partial enlarged view of the sagittal plane of the proximal-side clamp jaw according to the present invention is the same as that in FIG. 8. As shown in FIG. 8, after the clamp jaws clip target ablation tissue, air may be supplied to the air bag 34 to increase the pressure in the air bag 34. when the pressure in the air bag 34 is greater than the elastic restoring force of the elastic component 35, the air bag 34 pushes an ablation reagent injection head 55 and needle heads 47, 48 and 49 on it, so as to make the needle heads extend out of the clamp jaw. As mentioned before, injection needle heads may be installed according to the thickness of tissue in need of ablation, such that after the needle heads extend out of the clamp jaw, the length penetrated by needle tips of the needle heads into target ablation tissue differs, making sure that needle tips of the injection needle heads are able to penetrate into target ablation tissue at a depth that is deep enough for ablation but not deep enough to pierce target ablation tissue. A chemical ablation reagent may be transported by an ablation reagent supply device through a second pipeline 25 to needle heads installed in each needle fixing hole on the ablation reagent injection head, and injected into target ablation tissue via needle tips of needle heads. The obturator on the needle fixing hole 41 with no needle head installed and the obturator on its corresponding needle hole 40 are closed, so as to make sure that the chemical ablation reagent does not leak out via these unused needle holes. As shown in the figure, because the pipeline gradually expands at the side where an ablation reagent injection head 55 is connected, the pressure difference between each injection needle groove and injection needle heads installed therein can be narrowed when the chemical ablation reagent is received. In order to further balance the pressure of liquids in each needle head, a distributing board 57 as shown in FIG. 6 may be arranged at the expanded part of the second pipeline 25. When an ablation is finished, air in the air bag 34 is discharged, pressure in the air bag 34 decreases; when the pressure in the air bag 34 is lower than the elastic restoring force of the elastic component 35, the elastic assembly pushes the ablation reagent injection head 55 and each needle head installed thereon back inside the clamp jaw, the needle heads leave target ablation tissue, the clamp jaws on both sides are loosened, and the ablation apparatus may be removed from a body.

0.2-30.0 mm is optional for the length of needle tip of the needle head 28, and 0.8-2.2 mm preferable. The length of exposed needle tips may also be adjusted when the needle heads are installed in the needle fixing holes, so as to make sure that the depth at which the needle heads 28 penetrate into target tissue is deep enough for ablation but not deep enough to pierce the tissue. The needle heads 28 on the two clamp jaws 19 and 17 are at an angle of 30-150° with axes of the first pipeline 24 and the second pipeline 25 on their sagittal planes separately, and at an angle of 90° (i.e., perpendicular) preferably. In one embodiment, needle heads on the proximal-side clamp jaw 19 are at an angle of 30-90° with the axis of the first pipeline 24 on its sagittal plane, and injection needle heads on the distal-side clamp jaw 17 are at an angle of 90-150° with the axis of the second pipeline 25 on its sagittal plane; or injection needle heads on the distal-side clamp jaw 17 are at an angle of 30-90° with the axis of the second pipeline 25 on its sagittal plane, and injection needle heads on the proximal-side clamp jaw 19 are at an angle of 90-150° with the axis of the first pipeline 24 on its sagittal plane. The row length and number of needle heads 28 on the clamp jaws 17 and 19 can be determined by imaging methods or pre-clipping, as shown in FIG. 3.

FIG. 9 is a partial enlarged view of a sagittal plane of a distal-side clamp jaw in one embodiment for the chemical ablation apparatus according to the present invention. Unless otherwise specified, the partial enlarged view of the sagittal plane of the proximal-side clamp jaw according to the present invention is the same as that in FIG. 9. A needle fixing hole 42' as shown in FIG. 9 may also be provided on the ablation reagent injection head of the chemical ablation apparatus according to the present invention, on which a thread 59 is provided. As shown in the figure, a needle head 28' shows the structure of a needle head in an embodiment of the chemical ablation apparatus according to the present invention; one end of the needle 28', as shown in the figure, is a needle tip and the other a rear of needle head, with a thread 60 whose form matches that of the thread 59 on the needle fixing hole 42' provided on the rear of needle head. The length of injection needle heads to be installed may be determined according to the thickness of tissue in need of ablation, so as to make sure that the depth at which the needle heads penetrate into target ablation tissue is deep enough for ablation but not deep enough to pierce the target ablation tissue. The length of the needle heads is adjusted by the depth at which the thread 60 on the needle 28' screws in the thread 59, so as to adjust the necessary length at which the needle heads penetrate into target ablation tissue. In addition, FIG. 9 also illustrates a needle head extension and retraction control assembly of the chemical ablation apparatus according to the present invention. As shown in the figure, an electromagnetic elastic component 58 is provided between the ablation reagent injection head and injection needle holes, which is connected to an electronic control device (not marked) by a wire (not marked). As mentioned before, when the electromagnetic elastic component 58 is not energized, elastic restoring force of the electromagnetic spring presses the needle heads into the clamp jaw; when the electromagnetic elastic component 58 is energized, the electromagnetic elastic component contracts and generates an inward pull that drives the ablation reagent injection head to move towards the injection needle holes 41 until the needle heads extend out of the clamp jaw and penetrate into cardiac muscle tissue with a certain length.

Figure 10:
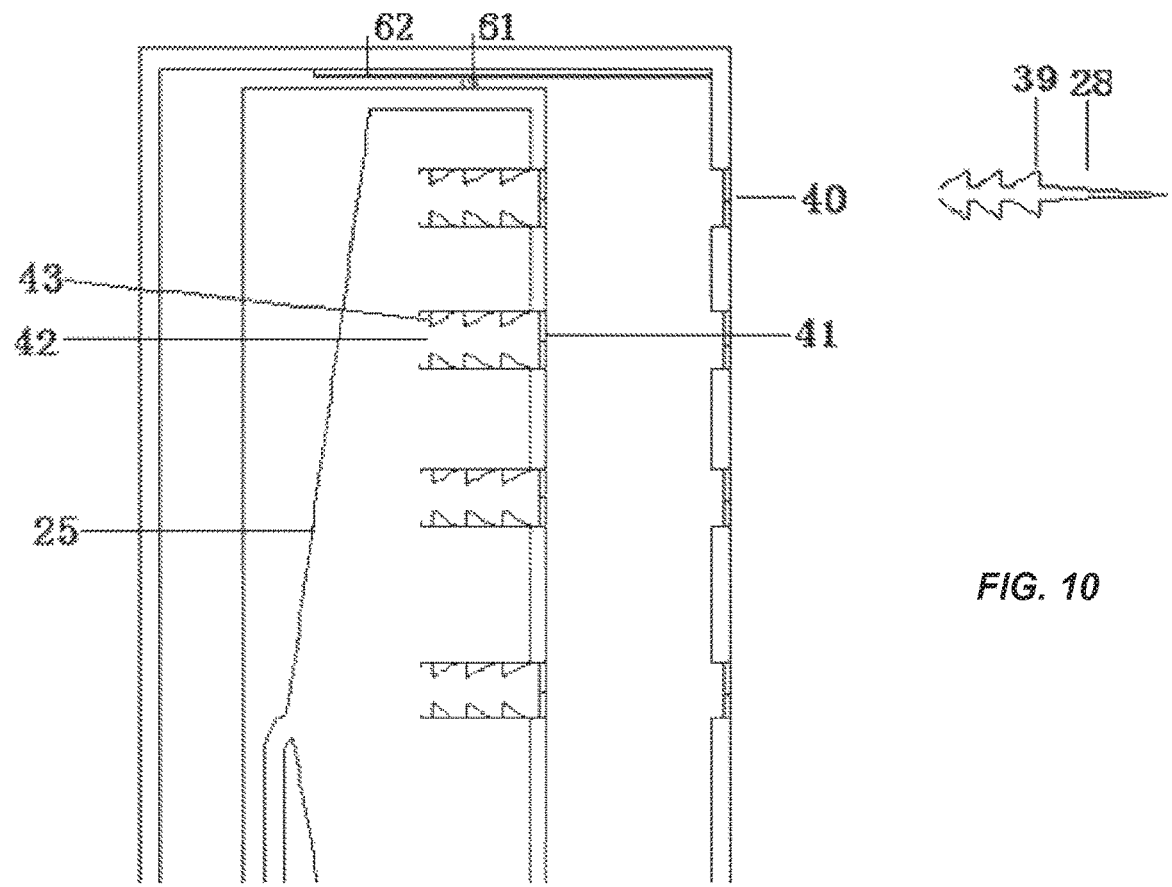
FIG. 10 is a partial enlarged view of a sagittal plane of a distal-side clamp jaw of the chemical ablation apparatus in one embodiment for the present invention.

FIG. 10 is a partial enlarged view of a sagittal plane of a distal-side clamp jaw in one embodiment for the chemical ablation apparatus according to the present invention. Unless otherwise specified, the partial enlarged view of the sagittal plane of the proximal-side clamp jaw according to the present invention is the same as that in FIG. 10. As shown in the figure, FIG. 10 illustrates a needle head extension and retraction control component of the chemical ablation apparatus according to the present invention. A linear stepper electric motor 61 is provided on the ablation reagent injection head and side wall of the clamp jaw (adjacent to the side of the clamp jaw where the injection needle holes is located) of the chemical ablation apparatus according to the present invention, which is connected to an electronic control device (not marked) by a wire (not marked). A threaded rod 62 of the linear stepper electric motor 61 is arranged on the side wall of the clamp jaw. When the electric motor rotates in one direction, it can drive the ablation reagent injection head to move away from the injection needle holes 41, such that the needle heads retract into the clamp jaw; when the electric motor rotates in an opposite direction, it can drive the ablation reagent injection head to move towards the injection needle holes 41 until the needle heads extend out of the clamp jaw and penetrate into cardiac muscle tissue with a certain length.

Figure 11:
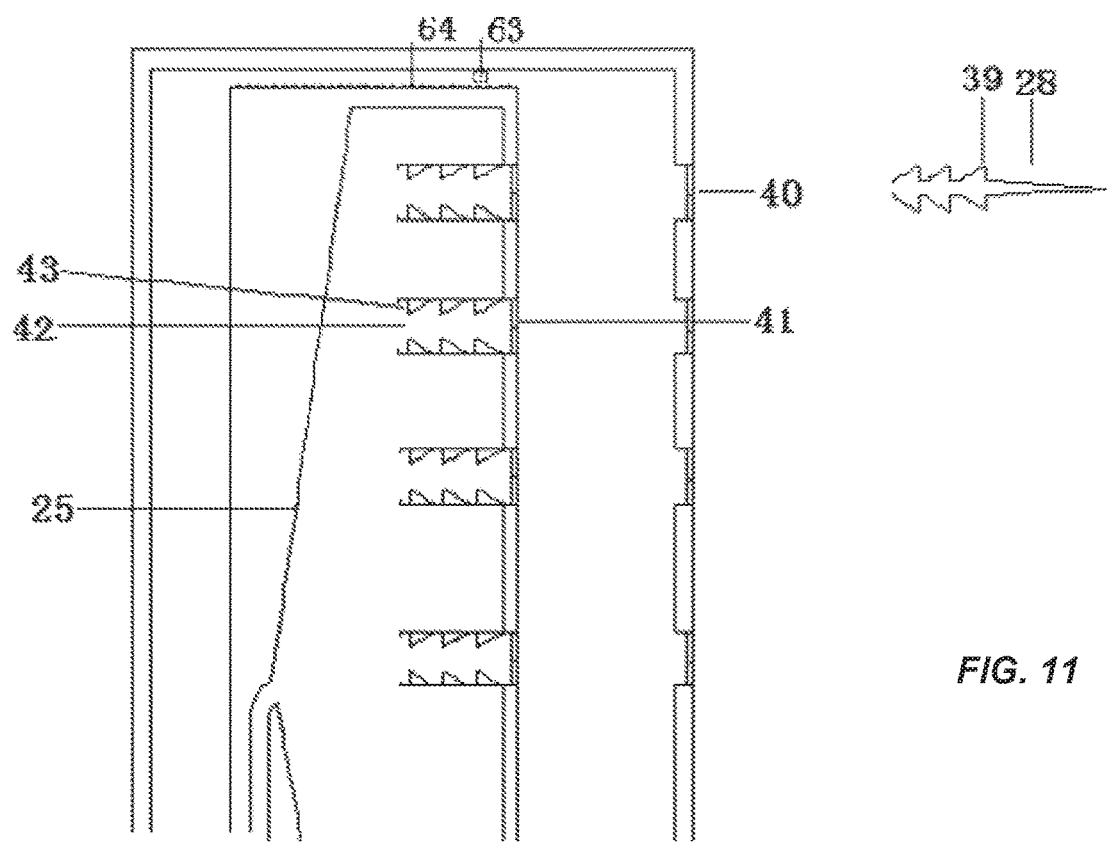
FIG. 11 is a partial enlarged view of a sagittal plane of a distal-side clamp jaw of the chemical ablation apparatus in one embodiment for the present invention.

FIG. 11 is a partial enlarged view of a sagittal plane of a distal-side clamp jaw in one embodiment for the chemical ablation apparatus according to the present invention. Unless otherwise specified, the partial enlarged view of the sagittal plane of the proximal-side clamp jaw according to the present invention is the same as that in FIG. 11. As shown in the figure, FIG. 11 illustrates a needle head extension and retraction control component of the chemical ablation apparatus according to the present invention. An electric motor 63 is provided on the side wall of the clamp jaw adjacent to the inner side of the clamp jaw (i.e., the side of the clamp jaw where the injection needle hole is located) of the chemical ablation apparatus according to the present invention, which is connected to a power supply (not marked) by a wire (not marked). A gear (not marked) is installed on the electric motor 63, and a gear rack 64 that engages with a first gear on the electric motor 63 is arranged on the side of the ablation reagent injection head that is close to the electric motor 63. When the electric motor 63 rotates in one direction, the gear engages with the gear rack 64 so as to drive the ablation reagent injection head to move away from the injection needle holes 41, such that the needle heads retract into the clamp jaw; when the electric motor 63 rotates in an opposite direction, the gear engages with the gear rack 64 so as to drive the ablation reagent injection head to move towards the injection needle holes 41 until the needle heads extend out of the clamp jaw and penetrate into cardiac muscle tissue with a certain length.

Figure 12A:
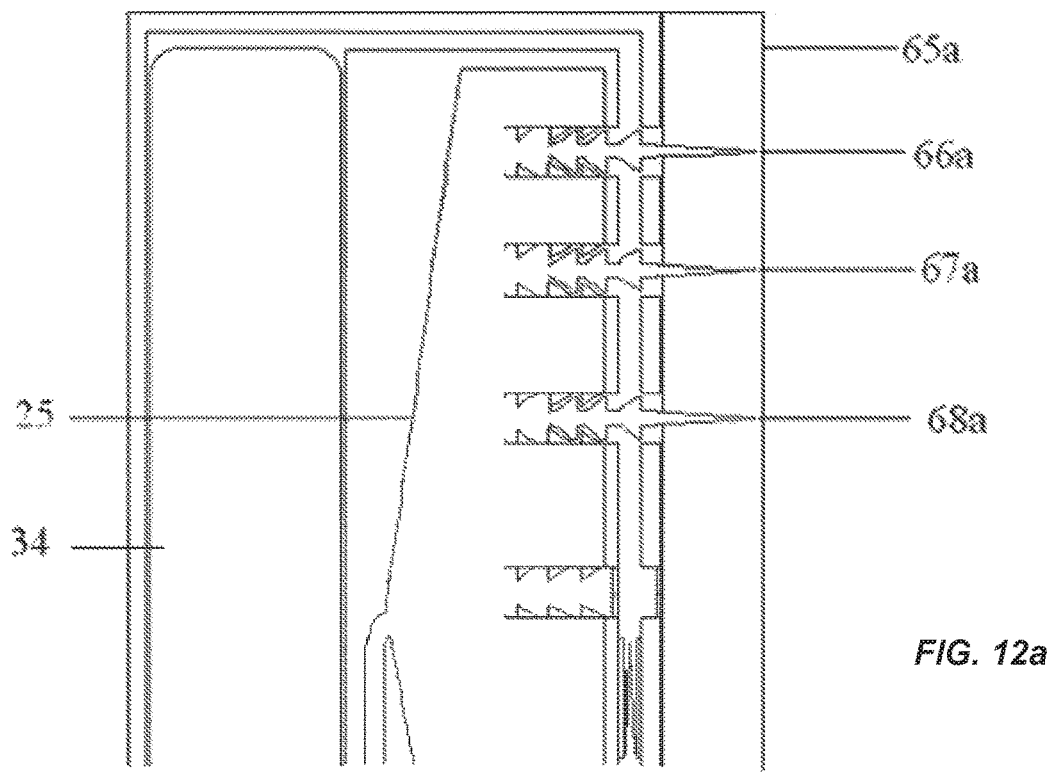
FIG. 12a is a partial enlarged view of a sagittal plane of a distal-side clamp jaw of the chemical ablation apparatus in one embodiment for the present invention. A cushion is arranged on one side of the clamp jaw.

FIG. 12a is a partial enlarged view of a sagittal plane of a distal-side clamp jaw in one embodiment for the chemical ablation apparatus according to the present invention (part of component is not marked). Unless otherwise specified, the partial enlarged view of the sagittal plane of the proximal-side clamp jaw according to the present invention is the same as that in FIG. 12a. As shown in FIG. 12a, a cushion 65a with proper thickness is arranged on the side of the clamp jaw with injection needle holes. The thickness of the cushion 65a is set as slightly greater than the length of injection needle heads 66a, 67a and 68a on the ablation clamp jaw when they fully extend, such that the injection needle heads remain inside the cushion 65a when they fully extend. By this way, when the ablation clamp is operated, the ablation clamp jaw can move in a body without puncturing surrounding tissue with injection needle heads 66a, 67a and 68a.

Figure 12B:
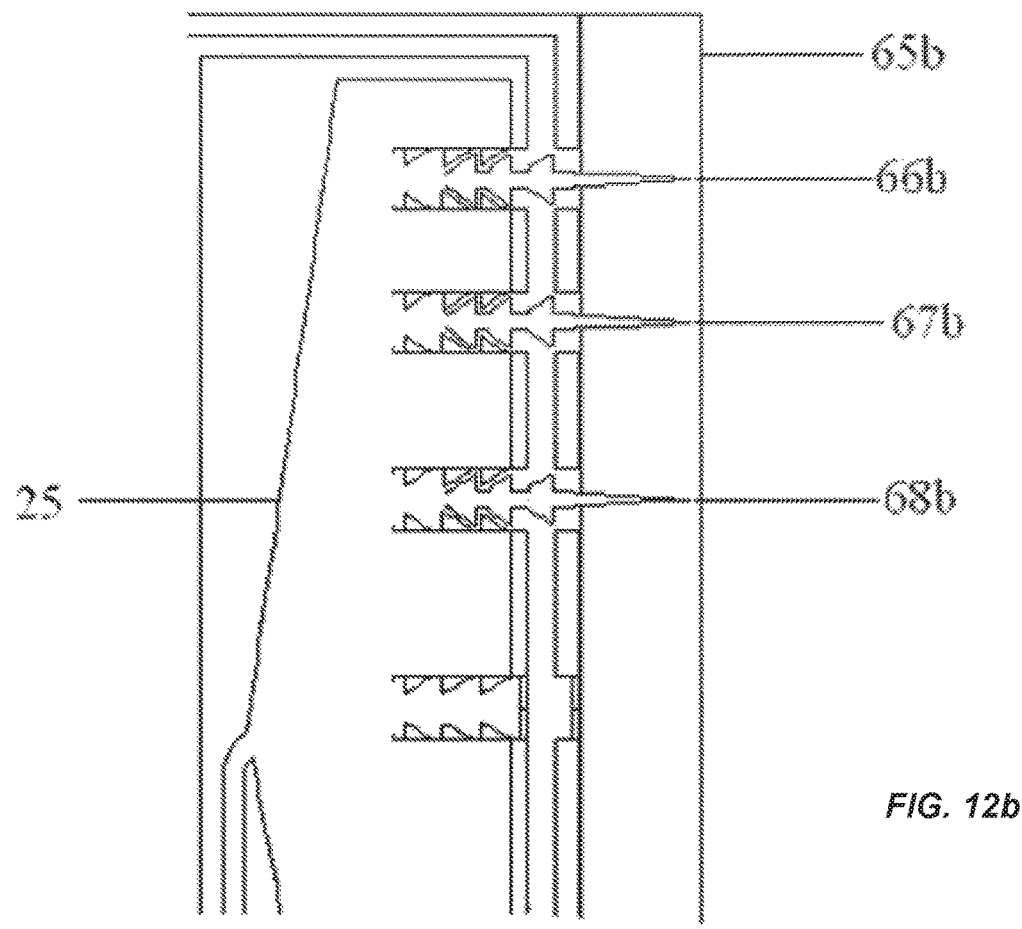
FIG. 12b is a partial enlarged view of a sagittal plane of a distal-side clamp jaw of the chemical ablation apparatus in one embodiment for the present invention. A cushion is arranged on one side of the clamp jaw.

FIG. 12b is a partial enlarged view of a sagittal plane of a distal-side clamp jaw in one embodiment for the chemical ablation apparatus according to the present invention (part of component is not marked). Unless otherwise specified, the partial enlarged view of the sagittal plane of the proximal-side clamp jaw according to the present invention is the same as that in FIG. 12b. As shown in FIG. 12b, needle heads on the chemical ablation apparatus according to the present invention is non-stretchable, and a cushion 65b with proper thickness is arranged on the side of the clamp jaw with injection needle holes. The thickness of the cushion 65b is set as slightly greater than the length of injection needle heads on the ablation clamp jaw, that is to say that when the clamp jaws on two sides are not clipping target ablation tissue, injection needle heads 66b, 67b and 68b are completely encased in the cushion 65b. By this way, when the ablation clamp is operated, the ablation clamp jaws can move in a body without puncturing surrounding tissue with injection needle heads 66b, 67b and 68b.

Figure 13A:
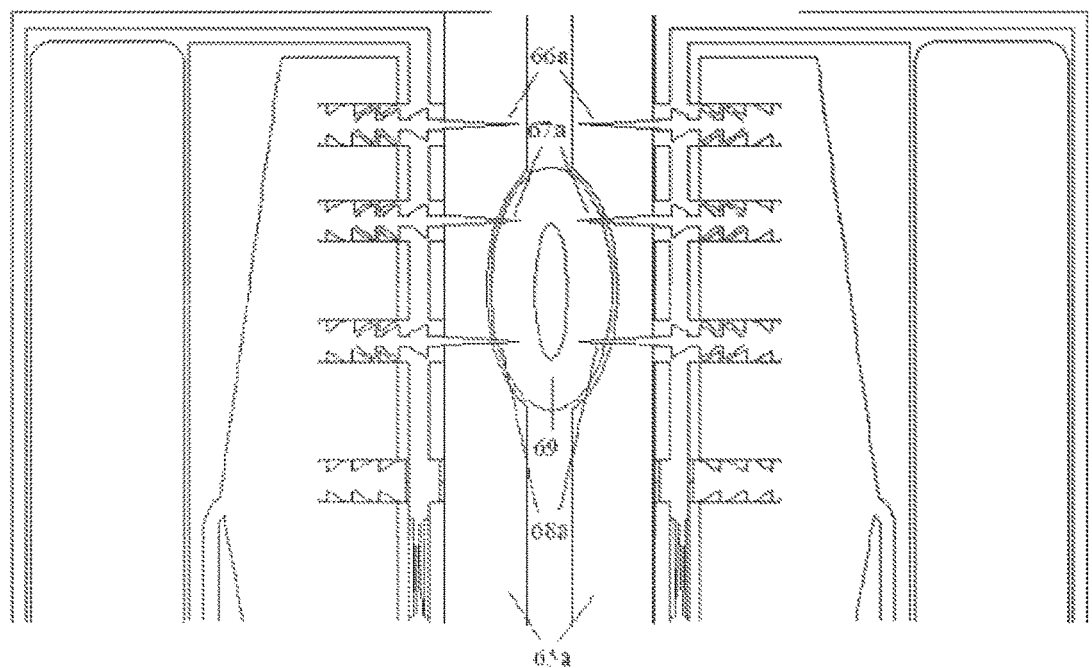
FIG. 13a is a partial enlarged view of a sagittal plane of clamp jaws on both sides clipping target ablation tissue in one embodiment for the chemical ablation apparatus according to the present invention.

FIG. 13a is a partial enlarged view of a sagittal plane of clamp jaws on both sides clipping target ablation tissue in one embodiment for the chemical ablation apparatus according to the present invention (part of component is not marked). As shown in FIG. 13a, a cushion 65a with proper thickness is arranged on the side of the clamp jaws with injection needle holes. The thickness of the cushion 65a is set as slightly greater than the length of fully extended injection needle heads 66a, 67a and 68a on the ablation clamp jaws. When the ablation clamp jaws clip target ablation tissue 69 and injection needle heads fully extend out of the clamp jaws, the cushion 65a is compressed at its portion that engages with the target ablation tissue due to the press of the ablation clamp jaws on two sides and target ablation tissue 69 between them, and injection needle heads 67a and 68a can extend out of the cushion 65a and then penetrate into target ablation tissue 69. And the injection needle 66a on the part of ablation clamp jaws that does not touch target ablation tissue 69 is still inside the cushion 65a. At this point, when a chemical ablation reagent is injected, injection needle heads 67a and 68a can inject the chemical ablation reagent into cardiac muscle tissue around the needle tips, while injection needle 66a cannot release the chemical ablation reagent because it is still inside the cushion 65a, thus avoiding the leak of the chemical ablation reagent from this part that damages surrounding tissue and prevents target ablation tissue from getting enough chemical ablation reagent.

Figure 13B:
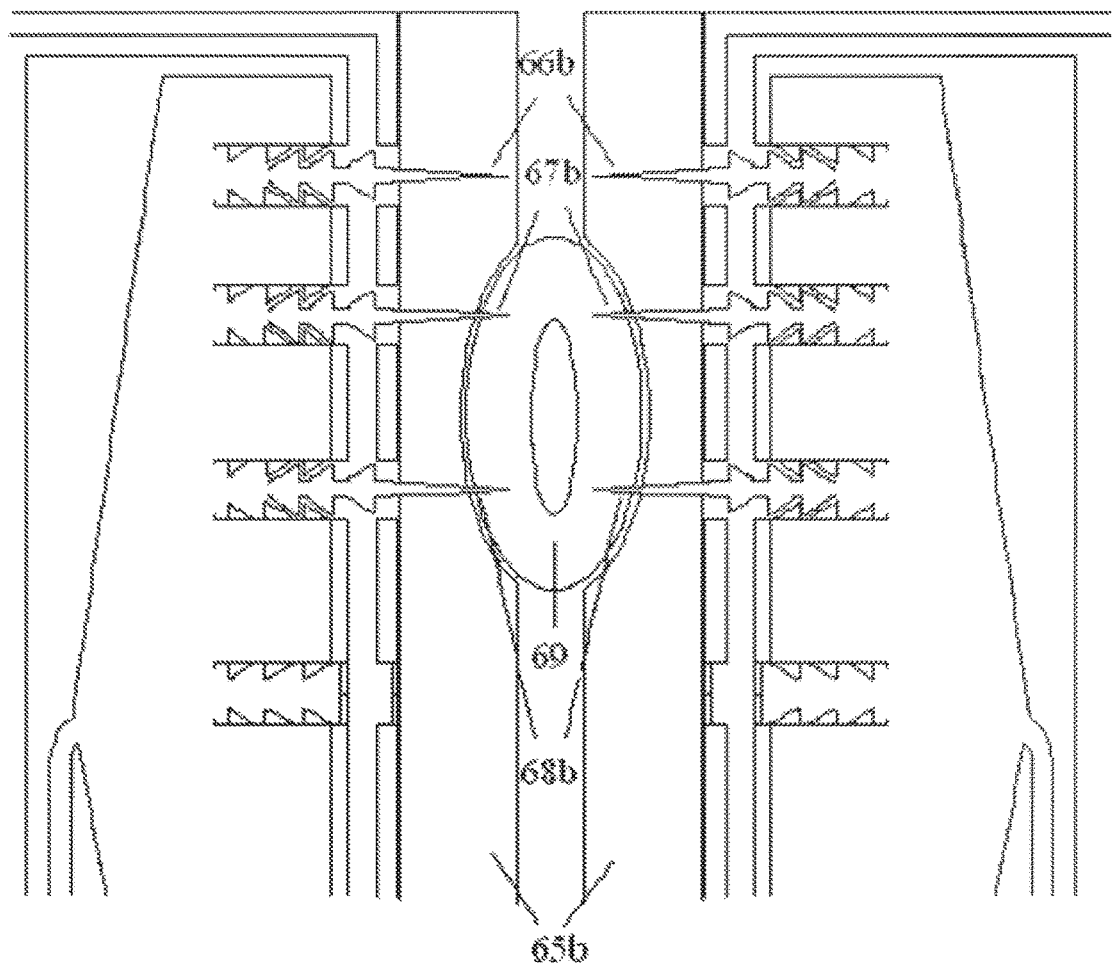
FIG. 13b is a partial enlarged view of a sagittal plane of clamp jaws on both sides clipping target ablation tissue in one embodiment for the chemical ablation apparatus according to the present invention.

FIG. 13b is a partial enlarged view of a sagittal plane of clamp jaws on both sides clipping target ablation tissue in one embodiment for the chemical ablation apparatus according to the present invention (part of component is not marked). As shown in FIG. 13b, injection needle heads on the chemical ablation apparatus according to the present invention is non-stretchable, and a cushion 65b with proper thickness is arranged on the side of the clamp jaws with injection needle holes. The thickness of the cushion 65b is set as slightly greater than the length of injection needle heads 66b, 67b and 68b on ablation clamp jaws, that is to say that when the clamp jaws on the two sides are not clipping target ablation tissue, injection needle heads 66b, 67b and 68b are fully encased in the cushion 65b; when ablation clamp jaws clips target ablation tissue 69, the cushion 65b is compressed at its portion that engages with the target ablation tissue due to the press of the ablation clamp jaws on the two sides and target ablation tissue 69 between them, and injection needle heads 67b and 68b extend out of the cushion 65b and then penetrate into target ablation tissue 69. And the injection needle 66b on the part of ablation clamp jaws that does not touch target ablation tissue 69 is still inside the cushion 65b. At this point, when a chemical ablation reagent is injected, injection needle heads 67b and 68b can inject the chemical ablation reagent into cardiac muscle tissue around the needle tips, while injection needle 66b cannot release the chemical ablation reagent because it is still inside the cushion 65b, thus avoiding the leak of the chemical ablation reagent from this part that damages surrounding tissue and prevents target ablation tissue from getting enough chemical ablation reagent.

Figure 14:
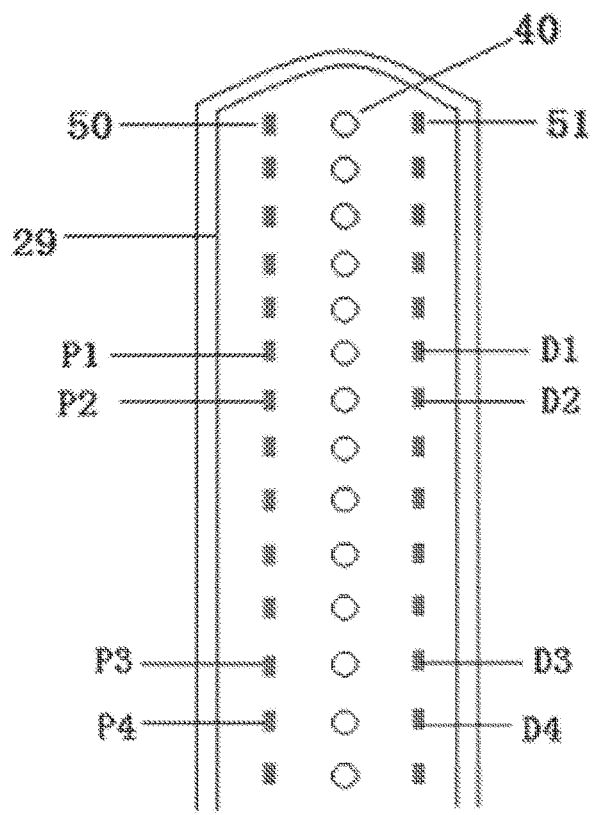
FIG. 14 is a partial enlarged view of a coronal plane of a clamp jaw on one side in one embodiment for the present invention.

FIG. 14 is a partial enlarged view of a coronal plane of a clamp jaw on one side in one embodiment for the present invention. FIG. 14 illustrates injection needle holes 40 arranged in a single row with equal spacing. A fence 29 may be provided on the clamp jaw. The fence 29 is located to both sides of the injection needle holes 40 and at the end of the distal end of the clamp jaw and extends towards needle tips of injection needle heads after they are installed. The height of the fence 29 is set as slightly greater or slightly smaller than or equal to the length of the needle tips of the needle heads in the lengthwise direction of the needle tips of the needle heads, preventing the needle tips of needle heads installed on the clamp jaws on both sides from touching one another when the clamp jaws on both sides come close and clip tissue. On both sides of injection needle holes on the clamp jaw and in parallel with and corresponding to the injection needle holes are provided with a proximal-side electrode 50 and a distal-side electrode 51 (the electrode is arranged on a cushion if there is any on the clamp jaw, and then when the injection needle heads penetrate out of the cushion, the electrode is close to the needle heads, for example, the electrode is outside the injection needle heads or on both sides of the injection needle heads, and is arranged in parallel with the injection needle heads). When the two clamp jaws clip target ablation tissue, each proximal-side electrode 50 and distal-side electrode 51 is closely attached to the surface of cardiac muscle tissue on both sides of target ablation tissue, such that mapping of electric activities of cardiac muscle tissue on both sides of target ablation tissue can be performed before, during and after ablation, and ablation effects can be verified.

Figure 15:
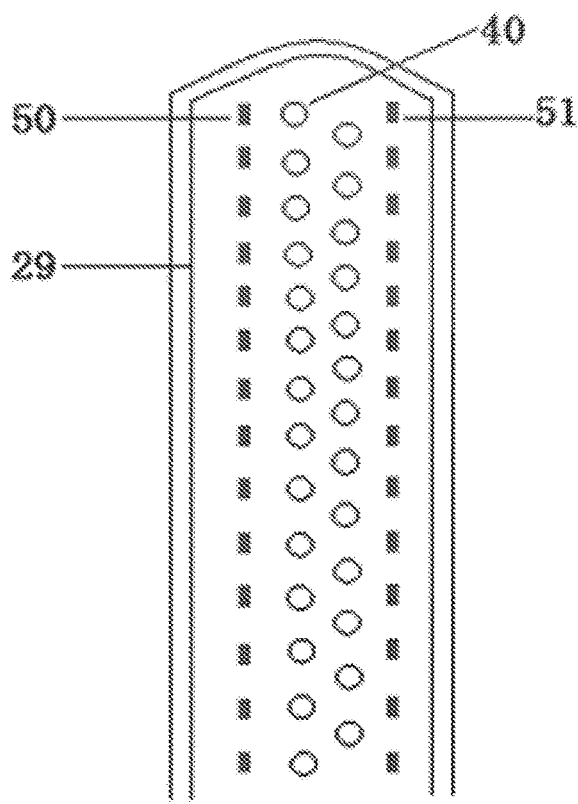
FIG. 15 is a partial enlarged view of a coronal plane of a clamp jaw on one side in another embodiment for the present invention.

FIG. 15 is a partial enlarged view of a coronal plane of a clamp jaw on one side in another embodiment for the present invention. FIG. 15 illustrates injection needle holes 40 arranged in two staggered rows with equal spacing. A fence 29 may be provided on the clamp jaw. The fence 29 is located to both sides of the injection needle holes 40 on the clamp jaw and at the end of the distal end of the clamp jaw and extends towards the needle tips of needle heads after they are installed. The height of the fence 29 is set as slightly greater or slightly smaller than or equal to the length of the needle tips of the needle heads in the lengthwise direction of the needle tips of the needle heads, preventing the needle tips of needle heads installed on the clamp jaws on both sides from touching one another when the clamp jaws on both sides come close and clip tissue. On both sides of injection needle holes on the clamp jaw and in parallel with and corresponding to the injection needle holes are provided with a proximal-side electrode 50 and a distal-side electrode 51 (the electrode is arranged on a cushion if there is any on the clamp jaw, and then when the injection needle heads penetrate out of the cushion, the electrode is close to the needle heads, for example, the electrode is outside the injection needle heads or on both sides of the injection needle heads, and is arranged in parallel with the injection needle heads). When the two clamp jaws clip target ablation tissue, each proximal-side electrode 50 and distal-side electrode 51 is closely attached to the surface of cardiac muscle tissue on both sides of target ablation tissue, such that mapping of electric activities of cardiac muscle tissue on both sides of target ablation tissue can be performed before, during and after ablation, and ablation effects can be verified.

Figure 16:
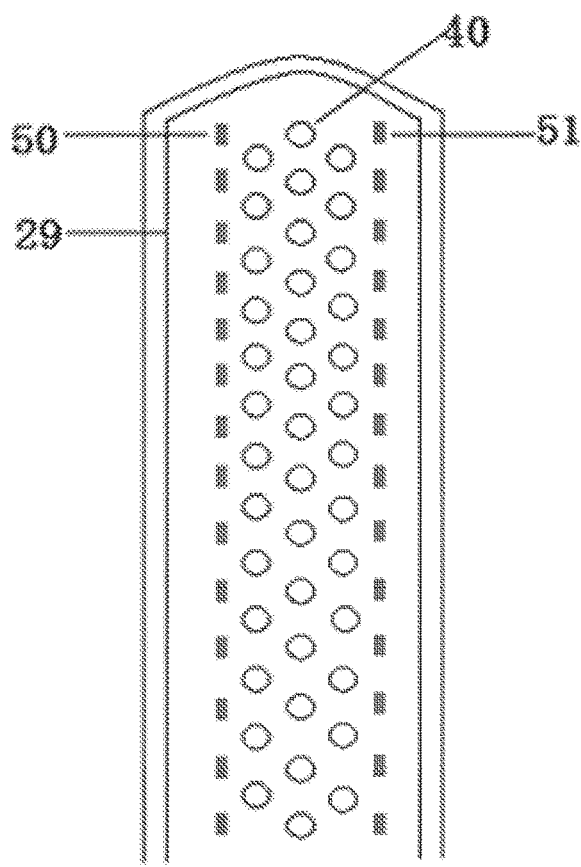
FIG. 16 is a partial enlarged view of a coronal plane of a clamp jaw on one side in another embodiment for the present invention.

FIG. 16 is a partial enlarged view of a coronal plane of a clamp jaw on one side in another embodiment for the present invention. FIG. 16 illustrates injection needle holes 40 arranged in three staggered rows with equal spacing. A fence 29 may be provided on the clamp jaw. The fence 29 is located to both sides of the injection needle holes 40 on the clamp jaw and at the end of the distal end of the clamp jaw and extends towards the needle tips of needle heads after they are installed. The height of the fence 29 is set as slightly greater or slightly smaller than or equal to the length of the needle tips of the needle heads in the lengthwise direction of the needle tips of the needle heads, preventing the needle tips of needle heads installed on the clamp jaws on both sides from touching one another when the clamp jaws on both sides come close and clip tissue. On both sides of injection needle holes on the clamp jaw and in parallel with and corresponding to the injection needle holes are provided with a proximal-side electrode 50 and a distal-side electrode 51 (the electrode is arranged on a cushion if there is any on the clamp jaw, and then when the injection needle heads penetrate out of the cushion, the electrode is close to the needle heads, for example, the electrode is outside the injection needle heads or on both sides of the injection needle heads, and is arranged in parallel with the injection needle heads). When the two clamp jaws clip target ablation tissue, each proximal-side electrode 50 and distal-side electrode 51 is closely attached to the surface of cardiac muscle tissue on both sides of target ablation tissue, such that mapping of electric activities of cardiac muscle tissue on both sides of target ablation tissue can be performed before, during and after ablation, and ablation effects can be verified.

In order to decrease or eliminate the occurrence rate of "gap" of target ablation tissue after it receives chemical ablation, in the ablation apparatus of the present invention, injection needle holes 40 on the two clamp jaws are arranged along the said pipeline with equal spacing in a single row (FIG. 14), two (FIG. 15) or multiple (FIG. 16) staggered rows separately.

As shown in FIG. 14, when the injection needle holes 40 on the two clamp jaws are arranged in one row with equal spacing, the spacing is set such that the damage areas in tissue caused by a chemical ablation reagent injected by two adjacent needle heads are able to at least overlap 1-40%, preferably 5-30%, and optimally 10-30%.

As shown in FIG. 15, when the injection needle holes 40 on the two clamp jaws are arranged in two staggered rows along the said pipeline separately, the spacing between two adjacent needle holes in each row is the same and is set such that the damage areas in tissue caused by a chemical ablation reagent injected by two adjacent needle heads in that row are able to at least overlap 1-30%, preferably 5-20%, and optimally 10-20%, and the spacing between one needle hole in one row and its adjacent needle hole in the other row is the same and is set such that the damage areas in tissue caused by a chemical ablation reagent injected by the two needle heads are able to at least overlap 1-30%, preferably 5-20%, and optimally 10-20%.

As shown in FIG. 16, when the injection needle holes 40 on the two clamp jaws are arranged in multiple staggered rows along the pipeline 25 separately, the spacing between two adjacent needle holes in each row is the same and is set such that the damage areas in tissue caused by a chemical ablation reagent injected by two adjacent needle heads in that row are able to at least overlap 1-30%, preferably 5-20%, and optimally 10-20%, and the spacing between one needle hole in one row and its adjacent needle hole in its adjacent row is the same and is set such that the damage areas in tissue caused by a chemical ablation reagent injected by the two needle heads are able to at least overlap 1-30%, preferably 5-20%, and optimally 10-20%.

The dosage of a chemical ablation reagent to be injected may be calculated by the calculation formula as follows: Total dosage of a chemical ablation reagent to be injected=threshold for reagent injection dosage of each needle head×number of needle heads, or when an injection pump is used: Time for injection of a chemical ablation reagent=(threshold for reagent injection dosage of each needle head×number of needle heads)/injection speed. The threshold for reagent injection dosage injected by each needle head refers to minimum or threshold enabling that: with the needle head as the center of a ball, the damage area (or volume) of ablated tissue caused by an injected chemical ablation reagent injected by the needle head overlaps with the damage area (or volume) caused by an adjacent needle head (as described above) so that no blind spot is left on the ablated tissue (i.e., no undamaged tissue is left). In practical use, reagent injection dosage of each needle head should be equal to or slightly greater than the threshold (generally controlled as about 10-40% greater than the threshold). The reagent injection dosage may be determined by animal test beforehand or determined based on experience of operators. For instance, when pulmonary vein and epicardium is ablated, threshold for reagent injection dosage of a needle head with a diameter of 0.25 mm is generally set as 3 ml, which is able to cause an approximately spherical tissue damage with the needle head as the center of the ball and a diameter of 14 mm at pulmonary vein antrum.

Figure 17:
FIG. 17 is a schematic view of electrocardiographic mapping based on an embodiment of the present invention.

FIG. 17 is a schematic view of electrocardiographic mapping based on an embodiment of the present invention. As mentioned above, according to the present invention, on both sides of injection needle holes in the ablation clamp jaws and in parallel with and corresponding to the injection needle holes are provided with a plurality of mapping electrodes, which are all connected to a wire and extend out of the clamp handle and can connect a display, a polygraph, a stimulator and other relevant equipment. This figure illustrates graph of cardiac electric activities around the target ablation tissue collected by mapping electrodes on the ablation clamp jaws. As shown in the figure, I, II, and III are limb leads graphs of body surface electrocardiogram detection, and P1-2, P3-4 are respectively electrocardiograms detected between proximal electrodes P1, P2 (FIG. 14) and between P3, P4 (FIG. 14) on the ablation clamp jaws. D1-2, D3-4 are respectively electrocardiograms detected between distal electrodes D1, D2 (FIG. 14) and between D3, D4 (FIG. 14) on the ablation clamp jaws. The graphs in the figure are detected before the ablation, atrial potential may be conducted via myocardium at proximal-side electrodes to myocardium at distal-side electrodes.

Figure 18:
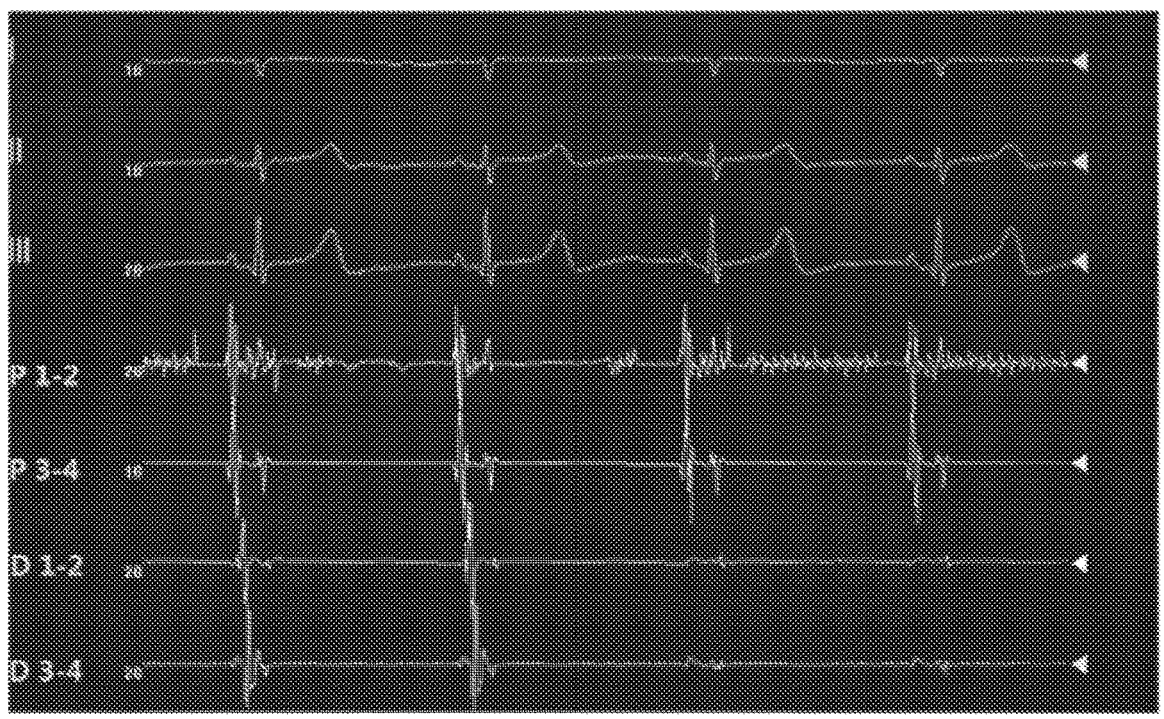
FIG. 18 is a schematic view of electrocardiographic mapping based on an embodiment of the present invention.

FIG. 18 is a schematic view of electrocardiographic mapping based on an embodiment of the present invention. As shown in the figure, I, II, and III are limb leads graphs of body surface electrocardiogram detection, and P1-2, P3-4 are respectively electrocardiograms detected between proximal electrodes P1, P2 and between P3, P4 on the ablation clamp jaws. D1-2, D3-4 are respectively electrocardiograms detected between distal electrodes D1, D2 and between D3, D4 on the ablation clamp jaws. The graphs in the figure are detected during the ablation, when potential at distal-side electrodes D1-D2, D3-D4 gradually disappear, i.e., atrial potential cannot be conducted via myocardium at proximal-side electrodes to myocardium at distal-side electrodes, indicating that the myocardium electrical conduction between the proximal-side electrodes P1-P2, P3-P4 and the distal-side electrodes D1-D2, D3-D4 are blocked, which means the chemical ablation takes effect.

Figure 19:
FIG. 19 is a schematic view of electrocardiographic mapping based on an embodiment of the present invention.

FIG. 19 is a schematic view of electrocardiographic mapping based on an embodiment of the present invention. As shown in the figure, I, II, and III are limb leads graphs of body surface electrocardiogram detection, and P1-2, P3-4 are respectively electrocardiograms detected between proximal electrodes P1, P2 and between P3, P4 on the ablation clamp jaws. D1-2, D3-4 are respectively electrocardiograms detected between distal electrodes D1, D2 and between D3, D4 on the ablation clamp jaws. The figure shows that when electrical stimulus is being released at the proximal-side electrodes P1-P2, the proximal-side electrodes P3-P4 on the same side of an ablation line are driven by the electrical stimulus while the distal-side electrodes D1-D2, D3-D4 on the opposite side of the ablation line can also map the electrical stimulus, indicating that partial electrical conduction still exists in myocardium between the proximal-side electrodes P1-P2, P3-P4 and the distal-side electrodes D1-D2, D3-D4, which means a "gap" caused by incomplete ablation may exist and a supplementary ablation is needed.

Figure 20:
FIG. 20 is a schematic view of electrocardiographic mapping based on an embodiment of the present invention.

FIG. 20 is a schematic view of electrocardiographic mapping based on an embodiment of the present invention. As shown in the figure, I, II, and III are limb leads graphs of body surface electrocardiogram detection, and P1-2, P3-4 are respectively electrocardiograms detected between proximal electrodes P1, P2 and between P3, P4 on the ablation clamp jaws. D1-2, D3-4 are respectively electrocardiograms detected between distal electrodes D1, D2 and between D3, D4 on the ablation clamp jaws. The figure shows that when electrical stimulus is being released at the distal-side electrodes D1-D2, the distal-side electrodes D3-D4 on the same side of an ablation line are driven by the electrical stimulus while the proximal-side electrodes P1-P2, P3-P4 on the opposite side of the ablation line can also map the electrical stimulus, indicating that partial electrical conduction still exists in myocardium between the proximal-side electrodes P1-P2, P3-P4 and the distal-side electrodes D1-P2, D3-P4, which means a "gap" caused by incomplete ablation may exist and a supplementary ablation is needed.

Figure 21:
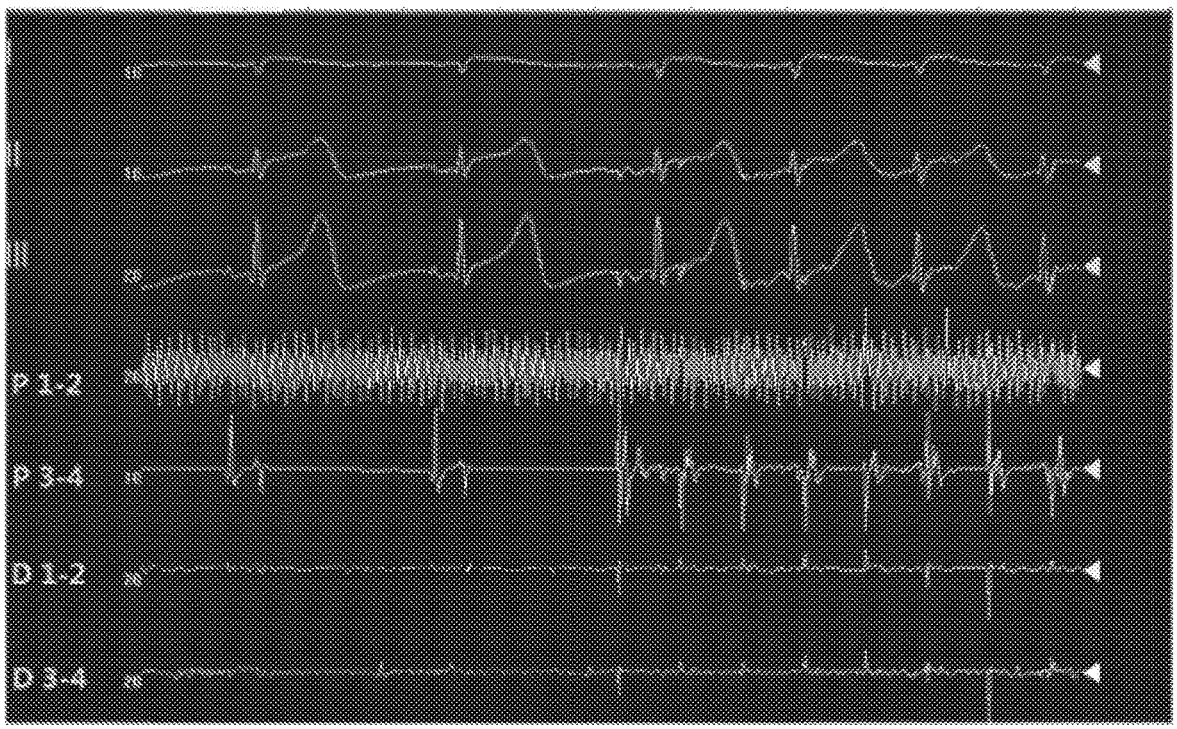
FIG. 21 is a schematic view of electrocardiographic mapping based on an embodiment of the present invention.

FIG. 21 is a schematic view of electrocardiographic mapping based on an embodiment of the present invention. As shown in the figure, I, II, and III are limb leads graphs of body surface electrocardiogram detection, and P1-2, P3-4 are respectively electrocardiograms detected between proximal electrodes P1, P2 and between P3, P4 on the ablation clamp jaws. D1-2, D3-4 are respectively electrocardiograms detected between distal electrodes D1, D2 and between D3, D4 on the ablation clamp jaws. The figure shows that after a supplementary ablation, electrical stimulus is released at the proximal-side electrodes P1-2, the proximal-side electrodes P3-4 on the same side of an ablation line are driven by the electrical stimulus while the distal-side electrodes D1-D2, D3-D4 on the opposite side of the ablation line cannot detect obvious electrical stimulus, indicating that almost no electrical conduction exists in myocardium between the proximal-side electrodes P1-P2, P3-P4 and the distal-side electrodes D1-D2, D3-D4, which means the ablation is complete.

Figure 22:
FIG. 22 is a schematic view of electrocardiographic mapping based on an embodiment of the present invention.

FIG. 22 is a schematic view of electrocardiographic mapping based on an embodiment of the present invention. As shown in the figure, I, II, and III are limb leads graphs of body surface electrocardiogram detection, and P1-2, P3-4 are respectively electrocardiograms detected between proximal electrodes P1, P2 and between P3, P4 on the ablation clamp jaws. D1-2, D3-4 are respectively electrocardiograms detected between distal electrodes D1, D2 and between D3, D4 on the ablation clamp jaws. The figure shows that after a supplementary ablation, electrical stimulus is released at the distal-side electrodes D1-D2, the distal-side electrodes D3-D4 on the same side of an ablation line are driven by the electrical stimulus while the proximal-side electrodes P1-P2, P3-P4 on the opposite side of the ablation line cannot detect electrical stimulus, indicating that almost no electrical conduction exists in myocardium between the proximal-side electrodes P1-P2, P3-P4 and the distal-side electrodes D1-D2, D3-D4, which means the ablation is complete.

Figure 23:
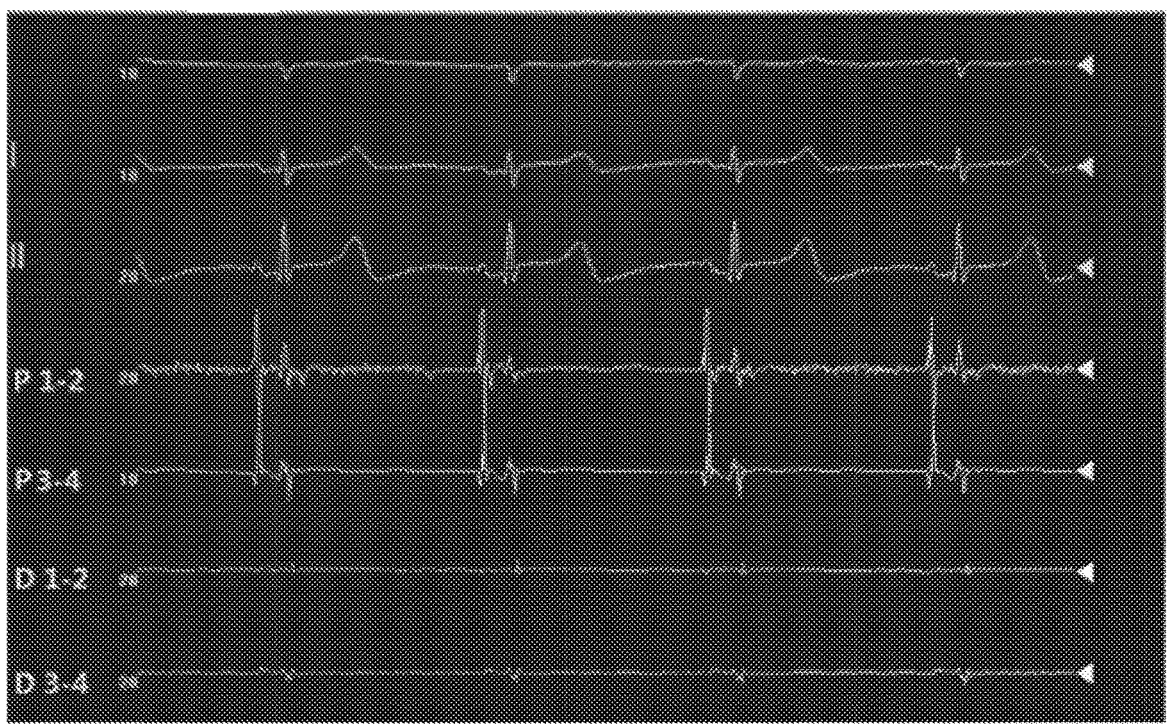
FIG. 23 is a schematic view of electrocardiographic mapping based on an embodiment of the present invention.

FIG. 23 is a schematic view of electrocardiographic mapping based on an embodiment of the present invention. As shown in the figure, I, II, and III are limb leads graphs of body surface electrocardiogram detection, and P1-2, P3-4 are respectively electrocardiograms detected between proximal electrodes P1, P2 and between P3, P4 on the ablation clamp jaws. D1-2, D3-4 are respectively electrocardiograms detected between distal electrodes D1, D2 and between D3, D4 on the ablation clamp jaws. The figure shows that after an ablation is finished, the proximal-side electrodes P1-P2, P3-P4 can map atrial potential while the distal-side electrodes D1-D2, D3-D4 cannot map atrial potential, i.e., atrial potential can be conducted to cardiac muscle tissue at the proximal-side electrodes P1-P2, P3-P4 but not cardiac muscle tissue at the distal-side electrodes D1-D2, D3-D4, indicating that after the ablation is finished, the ablation line is continuous and complete, which blocks cardiac electric activities' conduction via cardiac muscle tissue at the ablation line, and that the surgery is a success.

Given that analysis on cardiac electric activities is complicated and requires professional cardiac electrophysiology knowledge, in one embodiment of the present invention, the process including mapping, electrical stimulation and analysis of cardiac electric activities during an ablation may be programmed into one or more programs, which are configurated into an external equipment as software. The programs may be initiated after one ablation, which automatically finish the process of mapping, stimulation and analysis. Whether an ablation is complete, whether a supplementary ablation is needed and etc. can be concluded by the analysis on the process conducted by the software. If a supplementary ablation is necessary, the programs may be initiated again after the supplementary ablation is finished with the purpose of verifying the effect of ablation until the ablation succeeds. And the initiation of the verification programs may be set as a simple "one-click" initiation for verification program, and the verification result may also be shown in simple and plain display modes, such as words "ablation is incomplete, supplementary ablation is needed" and "ablation is complete", or red and green lights.

Detailed description of embodiments for the present invention is given with reference to the drawings, nevertheless, the present invention is not limited to the said embodiments. Components of the present invention may be utilized in any combination. With their knowledge, those commonly skilled in the art may make changes to the present invention provided that the purpose of the present invention is upheld.

The invention claimed is:

1. A chemical ablation apparatus, comprising:
   a clipping component comprising a clamp body and a clamp head, the clamp head comprising a pair of clamp jaws installed on the clamp body and configured to clamp or release a target ablation tissue by a relative motion of the clamp jaws;
   a needle head component installed inside the clamp jaws, the needle head component comprising a needle head assembly, and a needle head extension and retraction control assembly, wherein:
      the needle head extension and retraction control assembly comprises an ablation reagent injection head and a plurality of needle heads installed on the ablation reagent injection head;
      the plurality of needle heads are configured to be used to inject ablation reagents into the target ablation tissue;
      the needle head extension and retraction control assembly is configured to control the plurality of needle heads to extend out of or retract into the clamp jaws; and
      a plurality of injection needle holes provided on a side of each of the pair of clamp jaws opposite another of the pair of clamp jaws for the plurality of needle heads to extend out of or retract into the clamp jaws;
   a plurality of pipeline components comprising ablation reagent transporting pipelines, the ablation reagent transporting pipelines being in fluid communication with the needle head extension and retraction control assembly so as to transport the ablation reagents; and
   an electrocardiographic mapping component configured to detect a conduction condition of at least one of electrocardiosignals or external electrical stimulus signals around the target ablation tissue.

2. The chemical ablation apparatus of claim 1, wherein the needle head extension and retraction control assembly is further configured to control the plurality of needle heads to extend out of or retract into the clamp jaws by air pressure or hydraulic pressure.

3. The chemical ablation apparatus of claim 2, wherein the needle head extension and retraction control assembly comprises:
   an air bag or a liquid bag arranged on one side of the ablation reagent injection head that is distal from the plurality of injection needle holes; and
   an elastic component arranged between the ablation reagent injection head and the plurality of injection needle holes, wherein:
      a volume of the air bag or the liquid bag is changed by charging and discharging air or liquid, to thereby cause the ablation reagent injection head to move towards or away from the plurality of injection needle holes; and
      an elasticity of the elastic component is configured to cause the ablation reagent injection head to move away from the plurality of injection needle holes.

4. The chemical ablation apparatus of claim 1, wherein the needle head extension and retraction control assembly is configured to control the needle heads to extend out of or retract into the clamp jaws with electronic machinery.

5. The chemical ablation apparatus of claim 4, wherein: the needle head extension and retraction control assembly comprises an electromagnetic elastic component arranged between the ablation reagent injection head and the injection needle holes; and
   a length of the electromagnetic elastic component is controlled by an electric current, to thereby cause the ablation reagent injection head to move towards or away from the injection needle holes.

6. The chemical ablation apparatus of claim 4, wherein:
   the needle head extension and retraction control assembly comprises an electric motor provided inside the clamp jaws; and
   the electric motor is configured to cause the ablation reagent injection head to move towards or away from the injection needle holes with a transmission device.

7. The chemical ablation apparatus of claim 6, wherein the transmission device is at least one of a threaded rod or a gear.

8. The chemical ablation apparatus of claim 1, wherein:
   the chemical ablation apparatus further comprises a cushion arranged on the clamp jaws and covering the plurality of injection needle holes; and
   a thickness of the cushion is equal to or greater than a length of the plurality of needle heads in full extension.

9. The chemical ablation apparatus of claim 1, wherein the ablation reagent transporting pipelines have an enlarged flow area at a side where the ablation injection head is connected compared to a proximal portion of the ablation reagent transporting pipelines.

10. The chemical ablation apparatus of claim 9, wherein a distributing board is arranged at the expanded part of the ablation reagent transporting pipelines to balance the pressure of liquids in each needle head of the plurality of needle heads.

11. The chemical ablation apparatus of claim 1, wherein:
   each needle head of the plurality of needle heads comprises an independent pipeline at least on a side of the ablation reagent transporting pipeline that is proximal to the needle head; and
   an independent pipeline is configured to supply to one or more of the plurality of needle heads, respectively.

12. The chemical ablation apparatus of claim 1, wherein:
   the plurality of needle heads are installed on the ablation reagent injection head through needle fixing holes; and
   an installation depth of the needle heads into the needle fixing holes is adjustable.

13. The chemical ablation apparatus of claim 12, wherein a rear of the plurality of needle heads and the needle fixing holes have multiple-step structures of matching shapes.

14. The chemical ablation apparatus of claim 12, wherein a rear of the needle heads and the needle fixing holes have threads of matching shapes, to thereby adjust the installation depth.

15. The chemical ablation apparatus of claim 1, wherein head ends of needle tips of the plurality of needle heads are enclosed within holes arranged inside the clamp jaws.

16. The chemical ablation apparatus of claim 1, further comprising an electrocardiographic measurement device, wherein
   the electrocardiographic mapping component comprises mapping electrodes and a wire configured to connect the mapping electrodes to the electrocardiographic measurement device; and
   the electrocardiographic measurement device is configured to detect the conduction condition of at least one of the electrocardiosignals or external electrical stimulus signals around the target ablation tissue.

17. The chemical ablation apparatus of claim 16, wherein the mapping electrodes are arranged on the clamp jaws and arranged in parallel with the injection needle holes.

18. The chemical ablation apparatus of claim 1, wherein an angle between the clamp head and the clamp body is adjustable.

19. The chemical ablation apparatus of claim 18, wherein the clamp head and the clamp body are connected with a rotatable damping component.

20. The chemical ablation apparatus of claim 18, wherein:
the clamp head is connected to the clamp body with a rotatable component having a transmission device; and
the transmission device is configured to control the motion of the rotatable component under an external force.

21. The chemical ablation apparatus of claim 1, further comprising a spraying system and a suction system.

22. A chemical ablation apparatus, comprising:
a clipping component comprising a clamp body and a clamp head, the clamp head comprising a pair of clamp jaws installed on the clamp body and configured to clamp or release a target ablation tissue by a relative motion of the clamp jaws;
a needle head component installed inside the clamp jaws, the needle head component comprising a needle head assembly, and a needle head extension and retraction control assembly, wherein:
the needle head extension and retraction control assembly comprises an ablation reagent injection head and a plurality of needle heads installed on the ablation reagent injection head;
the plurality of needle heads are configured to be used to inject ablation reagents into the target ablation tissue;
the needle head extension and retraction control assembly is configured to control the plurality of needle heads to extend out of or retract into the clamp jaws; and
a plurality of injection needle holes provided on a side of each of the pair of clamp jaws opposite another of the pair of clamp jaws for the plurality of needle heads to extend out of or retract into the clamp jaws;
a plurality of pipeline components comprising ablation reagent transporting pipelines, the ablation reagent transporting pipelines being in fluid communication with the needle head extraction and retraction control assembly so as to transport the ablation reagents;
an electrocardiographic mapping component configured to detect a conduction condition of at least one of electrocardiosignals or external electrical stimulus signals around the target ablation tissue;
a spraying system comprising spraying holes arranged on the clamp jaws; and
a suction system comprising suction holes arranged on the clamp jaws, wherein the spraying holes and the suction holes are connected to a spraying pipeline and a suction pipeline, respectively.

23. A chemical ablation apparatus, comprising:
a clipping component comprising a clamp body and a clamp head, the clamp head comprising a pair of clamp jaws installed on the clamp body and configured to clamp or release a target ablation tissue by a relative motion of the clamp jaws;
a needle head component installed inside the clamp jaws, the needle head component comprising a needle head assembly, and a needle head extension and retraction control assembly, wherein:
the needle head extension and retraction control assembly comprises an ablation reagent injection head and a plurality of needle heads installed on the ablation reagent injection head;
the plurality of needle heads are configured to be used to inject ablation reagents into the target ablation tissue;
the needle head extension and retraction control assembly is configured to control the plurality of needle heads to extend out of or retract into the clamp jaws; and
a plurality of injection needle holes provided on a side of each of the pair of clamp jaws opposite another of the pair of clamp jaws for the plurality of needle heads to extend out of or retract into the clamp jaws;
a plurality of pipeline components comprising ablation reagent transporting pipelines, the ablation reagent transporting pipelines being in fluid communication with the needle head extension and retraction control assembly so as to transport the ablation reagents;
an electrocardiographic mapping component configured to detect a conduction condition of at least one of electrocardiosignals or external electrical stimulus signals around the target ablation tissue; and
a pulley, around which at least one of the pipeline components is wound, wherein an extension or retraction of at least one of the pipeline components is adjusted by decreasing or increasing a number of windings of the at least one of the pipeline components that is wound to adapt to the motion of the clamp head.

24. The chemical ablation apparatus of claim 1, further comprising a fence arranged on both sides of the plurality of injection needle holes in the clamp jaws and at a distal end of the clamp jaws, the fence extending in the same direction as the plurality of needle heads.

* * * * *